United States Patent
Perricone

(10) Patent No.: US 9,968,634 B2
(45) Date of Patent: *May 15, 2018

(54) TECHNIQUES AND SYSTEMS FOR TREATMENT OF NEUROPATHIC PAIN AND OTHER INDICATIONS

(71) Applicant: Transdermal Biotechnology, Inc., Meriden, CT (US)

(72) Inventor: Nicholas V. Perricone, Madison, CT (US)

(73) Assignee: Transdermal Biotechnology, Inc., Meriden, CT (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/281,971

(22) Filed: Sep. 30, 2016

(65) Prior Publication Data
US 2017/0080019 A1    Mar. 23, 2017

Related U.S. Application Data

(63) Continuation of application No. 14/924,651, filed on Oct. 27, 2015, now Pat. No. 9,480,711, which is a continuation of application No. 14/492,279, filed on Sep. 22, 2014, now Pat. No. 9,198,932, which is a continuation of application No. 13/801,313, filed on Mar. 13, 2013, now Pat. No. 8,871,259, which is a continuation-in-part of application No. 13/623,027, filed on Sep. 19, 2012.

(51) Int. Cl.
| | |
|---|---|
| A61K 33/00 | (2006.01) |
| A61K 47/10 | (2017.01) |
| A61K 47/14 | (2017.01) |
| A61K 31/685 | (2006.01) |
| A61K 9/127 | (2006.01) |
| A61K 9/50 | (2006.01) |
| A61K 9/00 | (2006.01) |
| A61K 9/10 | (2006.01) |
| A61K 47/24 | (2006.01) |
| A61K 9/06 | (2006.01) |
| A61K 47/22 | (2006.01) |
| A61K 47/54 | (2017.01) |
| A61K 47/69 | (2017.01) |
| A61K 47/18 | (2017.01) |

(52) U.S. Cl.
CPC ............ *A61K 33/00* (2013.01); *A61K 9/0014* (2013.01); *A61K 9/06* (2013.01); *A61K 9/10* (2013.01); *A61K 9/127* (2013.01); *A61K 9/50* (2013.01); *A61K 31/685* (2013.01); *A61K 47/10* (2013.01); *A61K 47/14* (2013.01); *A61K 47/22* (2013.01); *A61K 47/24* (2013.01); *A61K 47/544* (2017.08); *A61K 47/6911* (2017.08); *A61K 47/186* (2013.01)

(58) Field of Classification Search
CPC ............ A61K 2800/75; A61K 2800/88; A61K 31/16; A61K 31/165; A61K 8/33; A61K 8/42; A61K 8/44; A61K 8/8152; A61K 8/86; A61K 9/0014; A61K 9/7084; A61K 33/00; A61K 47/6911; A61K 47/544; A61K 47/10; A61K 47/14; A61K 47/22; A61K 9/06; A61K 31/685; A61K 47/24; A61K 9/10; A61K 9/50; A61K 9/127; A61K 47/186; A61Q 17/00; A61Q 19/10
See application file for complete search history.

(56) References Cited

U.S. PATENT DOCUMENTS

| | | | |
|---|---|---|---|
| 4,174,296 | A | 11/1979 | Kass |
| 4,333,927 | A | 6/1982 | Ofuchi et al. |
| 4,614,730 | A | 9/1986 | Hansen et al. |
| 4,624,665 | A | 11/1986 | Nuwayser |
| 4,687,661 | A | 8/1987 | Kikuchi et al. |
| 4,708,861 | A | 11/1987 | Popescu et al. |
| 4,743,449 | A | 5/1988 | Yoshida et al. |
| 5,120,561 | A | 6/1992 | Silvia et al. |

(Continued)

FOREIGN PATENT DOCUMENTS

| | | |
|---|---|---|
| CA | 2182390 A1 | 8/1995 |
| CA | 2181390 A1 | 1/1997 |

(Continued)

OTHER PUBLICATIONS

U.S. Appl. No. 15/343,402, filed Nov. 4, 2016, Perricone.

(Continued)

*Primary Examiner* — Snigdha Maewall
(74) *Attorney, Agent, or Firm* — Wolf, Greenfield & Sacks, P.C.

(57) ABSTRACT

The present invention generally relates to compositions and methods for treatment of subjects having or at risk of neuropathic pain or other conditions. In some cases, the composition may include nitric oxide. The nitric oxide may be present within a first phase comprising a lecithin, such as phosphatidylcholine. In certain embodiments, the lecithin is present in liposomes, micelles, or other vesicles containing nitric oxide. The composition can take the form of a gel, a cream, a lotion, an ointment, a solution, a solid "stick," etc., that can be rubbed or sprayed onto the skin, e.g., onto a location with neuropathic pain, or on another suitable portion of the skin. Other aspects of the present invention are generally directed to methods of making or using such compositions, methods of promoting such compositions, kits including such compositions, or the like.

20 Claims, 1 Drawing Sheet

(56) References Cited

U.S. PATENT DOCUMENTS

| | | |
|---|---|---|
| 5,151,272 A | 9/1992 | Engstrom et al. |
| 5,206,219 A | 4/1993 | Desai |
| 5,254,348 A | 10/1993 | Hoffman et al. |
| 5,380,761 A | 1/1995 | Szabo et al. |
| 5,391,548 A | 2/1995 | Francoeur et al. |
| 5,439,967 A | 8/1995 | Mathur |
| 5,476,651 A | 12/1995 | Meybeck et al. |
| 5,484,816 A | 1/1996 | Yanagida et al. |
| 5,504,117 A | 4/1996 | Gorfine |
| 5,550,263 A | 8/1996 | Herslof et al. |
| 5,576,016 A | 11/1996 | Amselem et al. |
| 5,656,286 A | 8/1997 | Miranda et al. |
| 5,662,932 A | 9/1997 | Amselem et al. |
| 5,674,912 A | 10/1997 | Martin |
| 5,693,676 A | 12/1997 | Gorfine |
| 5,726,164 A | 3/1998 | Weder et al. |
| 5,753,259 A | 5/1998 | Engstrom et al. |
| 5,776,494 A | 7/1998 | Guskey et al. |
| 5,807,573 A | 9/1998 | Ljusberg-Wahren et al. |
| 5,814,666 A | 9/1998 | Green et al. |
| 5,858,398 A | 1/1999 | Cho |
| 5,869,539 A | 2/1999 | Garfield et al. |
| 5,874,479 A | 2/1999 | Martin |
| 5,879,690 A | 3/1999 | Perricone |
| 5,891,472 A | 4/1999 | Russell |
| 5,955,502 A | 9/1999 | Hansen et al. |
| 5,976,562 A | 11/1999 | Krall et al. |
| 5,985,298 A | 11/1999 | Brieva et al. |
| 6,022,561 A | 2/2000 | Carlsson et al. |
| 6,045,827 A | 4/2000 | Russell |
| 6,103,275 A | 8/2000 | Seitz et al. |
| 6,133,320 A | 10/2000 | Yallampalli et al. |
| 6,165,500 A | 12/2000 | Cevc |
| 6,191,121 B1 | 2/2001 | Perricone |
| 6,193,997 B1 | 2/2001 | Modi |
| 6,207,713 B1 | 3/2001 | Fossel |
| 6,211,250 B1 | 4/2001 | Tomlinson et al. |
| 6,214,375 B1 | 4/2001 | Modi |
| 6,242,099 B1 | 6/2001 | Grandmontagne et al. |
| 6,287,601 B1 | 9/2001 | Russell |
| 6,294,192 B1 | 9/2001 | Patel et al. |
| 6,391,869 B1 | 5/2002 | Parks et al. |
| 6,458,841 B2 | 10/2002 | Fossel |
| 6,464,987 B1 | 10/2002 | Fanara et al. |
| 6,521,250 B2 | 2/2003 | Meconi et al. |
| 6,538,061 B2 | 3/2003 | Chaiyawat et al. |
| 6,555,573 B2 | 4/2003 | Rosenbloom |
| 6,780,849 B2 | 8/2004 | Herrmann et al. |
| 6,932,963 B2 | 8/2005 | Perricone |
| 6,936,044 B2 | 8/2005 | McDaniel |
| 7,033,574 B1 | 4/2006 | Schneider et al. |
| 7,182,956 B2 | 2/2007 | Perricone et al. |
| 7,189,761 B2 | 3/2007 | Gorfine |
| 7,696,247 B2 | 4/2010 | Herrmann et al. |
| 7,820,420 B2 | 10/2010 | Whitlock |
| 7,976,743 B2 | 7/2011 | Huang et al. |
| 8,273,711 B2 | 9/2012 | Perricone |
| 8,435,942 B2 | 5/2013 | Perricone et al. |
| 8,668,937 B2 | 3/2014 | Perricone et al. |
| 8,871,254 B2 | 10/2014 | Perricone |
| 8,871,255 B2 | 10/2014 | Perricone |
| 8,871,256 B2 | 10/2014 | Perricone |
| 8,871,257 B2 | 10/2014 | Perricone |
| 8,871,258 B2 | 10/2014 | Perricone |
| 8,871,259 B2 | 10/2014 | Perricone |
| 8,871,260 B2 | 10/2014 | Perricone |
| 8,871,261 B2 | 10/2014 | Perricone |
| 8,871,262 B2 | 10/2014 | Perricone |
| 9,198,853 B2 | 12/2015 | Perricone |
| 9,198,854 B2 | 12/2015 | Perricone |
| 9,198,930 B2 | 12/2015 | Perricone |
| 9,198,931 B2 | 12/2015 | Perricone |
| 9,198,932 B2 | 12/2015 | Perricone |
| 9,198,933 B2 | 12/2015 | Perricone |
| 9,198,970 B2 | 12/2015 | Perricone |
| 9,205,043 B2 | 12/2015 | Perricone |
| 9,295,638 B2 | 3/2016 | Perricone |
| 9,480,705 B2 | 11/2016 | Perricone |
| 9,480,706 B2 | 11/2016 | Perricone |
| 9,480,707 B2 | 11/2016 | Perricone |
| 9,480,708 B2 | 11/2016 | Perricone |
| 9,480,709 B2 | 11/2016 | Perricone |
| 9,480,710 B2 | 11/2016 | Perricone |
| 9,480,711 B2 | 11/2016 | Perricone |
| 9,517,179 B2 | 12/2016 | Perricone |
| 2002/0131994 A1 | 9/2002 | Schur et al. |
| 2002/0153509 A1 | 10/2002 | Lynch et al. |
| 2002/0160040 A1 | 10/2002 | Spicer et al. |
| 2002/0182162 A1 | 12/2002 | Shahinpoor et al. |
| 2004/0018237 A1 | 1/2004 | Perricone |
| 2004/0096494 A1 | 5/2004 | Siekmann et al. |
| 2004/0191305 A1 | 9/2004 | Perricone et al. |
| 2004/0197391 A1 | 10/2004 | Perricone et al. |
| 2005/0074468 A1 | 4/2005 | Kim et al. |
| 2005/0074506 A1 | 4/2005 | Natan et al. |
| 2005/0226945 A1 | 10/2005 | Ruwart |
| 2006/0105955 A1 | 5/2006 | Perricone |
| 2006/0127469 A1 | 6/2006 | Perricone et al. |
| 2006/0275353 A1 | 12/2006 | Perricone et al. |
| 2007/0065473 A1 | 3/2007 | Miller |
| 2008/0153789 A1 | 6/2008 | Dmowski et al. |
| 2008/0175893 A1 | 7/2008 | Huang et al. |
| 2008/0234239 A1* | 9/2008 | Wheeler ............. A61K 9/0014 514/167 |
| 2009/0214624 A1 | 8/2009 | Smith et al. |
| 2009/0304815 A1 | 12/2009 | Cossu et al. |
| 2009/0324698 A1 | 12/2009 | Wagner et al. |
| 2010/0048520 A1 | 2/2010 | Safdi et al. |
| 2010/0196461 A1 | 8/2010 | Simpkins |
| 2010/0292139 A1 | 11/2010 | Perricone |
| 2010/0311696 A1 | 12/2010 | Perricone |
| 2011/0104240 A1 | 5/2011 | Jones et al. |
| 2011/0123577 A1 | 5/2011 | Perricone et al. |
| 2012/0156163 A1 | 6/2012 | Bauman et al. |
| 2013/0029989 A1 | 1/2013 | Coderre et al. |
| 2013/0059017 A1 | 3/2013 | Perricone et al. |
| 2014/0079679 A1 | 3/2014 | Perricone |
| 2014/0079761 A1 | 3/2014 | Perricone |
| 2014/0079762 A1 | 3/2014 | Perricone |
| 2014/0079763 A1 | 3/2014 | Perricone |
| 2014/0079764 A1 | 3/2014 | Perricone |
| 2014/0079765 A1 | 3/2014 | Perricone |
| 2014/0079766 A1 | 3/2014 | Perricone |
| 2014/0079767 A1 | 3/2014 | Perricone |
| 2014/0079768 A1 | 3/2014 | Perricone |
| 2014/0105963 A1 | 4/2014 | Perricone et al. |
| 2014/0271730 A1 | 9/2014 | Perricone |
| 2014/0271731 A1 | 9/2014 | Perricone |
| 2014/0271732 A1 | 9/2014 | Perricone |
| 2014/0271742 A1 | 9/2014 | Perricone |
| 2014/0271743 A1 | 9/2014 | Perricone |
| 2014/0271800 A1 | 9/2014 | Perricone |
| 2014/0271801 A1 | 9/2014 | Perricone |
| 2014/0271802 A1 | 9/2014 | Perricone |
| 2014/0271803 A1 | 9/2014 | Perricone |
| 2014/0271804 A1 | 9/2014 | Perricone |
| 2014/0271805 A1 | 9/2014 | Perricone |
| 2014/0271806 A1 | 9/2014 | Perricone |
| 2014/0271807 A1 | 9/2014 | Perricone |
| 2014/0271808 A1 | 9/2014 | Perricone |
| 2014/0271809 A1 | 9/2014 | Perricone |
| 2014/0271810 A1 | 9/2014 | Perricone |
| 2014/0271811 A1 | 9/2014 | Perricone |
| 2014/0271934 A1 | 9/2014 | Perricone |
| 2014/0271935 A1 | 9/2014 | Perricone |
| 2014/0271936 A1 | 9/2014 | Perricone |
| 2014/0271937 A1 | 9/2014 | Perricone |
| 2014/0271938 A1 | 9/2014 | Perricone |
| 2015/0004196 A1 | 1/2015 | Perricone |
| 2015/0010655 A1 | 1/2015 | Perricone |
| 2015/0010656 A1 | 1/2015 | Perricone |
| 2015/0010657 A1 | 1/2015 | Perricone |
| 2015/0010658 A1 | 1/2015 | Perricone |
| 2015/0010659 A1 | 1/2015 | Perricone |

(56) References Cited

U.S. PATENT DOCUMENTS

| | | |
|---|---|---|
| 2015/0010660 A1 | 1/2015 | Perricone |
| 2015/0010661 A1 | 1/2015 | Perricone |
| 2015/0010662 A1 | 1/2015 | Perricone |
| 2015/0122818 A1* | 5/2015 | Bruna .............. B65D 51/1605 220/345.6 |
| 2016/0045537 A1 | 2/2016 | Perricone |
| 2016/0045538 A1 | 2/2016 | Perricone |
| 2016/0045539 A1 | 2/2016 | Perricone |
| 2016/0045540 A1 | 2/2016 | Perricone |
| 2016/0045541 A1 | 2/2016 | Perricone |
| 2016/0045542 A1 | 2/2016 | Perricone |
| 2016/0045543 A1 | 2/2016 | Perricone |
| 2016/0045544 A1 | 2/2016 | Perricone |
| 2016/0067174 A9 | 3/2016 | Perricone |
| 2016/0136169 A1 | 5/2016 | Perricone |
| 2016/0158276 A1 | 6/2016 | Perricone |
| 2017/0080016 A1 | 3/2017 | Perricone |
| 2017/0080017 A1 | 3/2017 | Perricone |
| 2017/0080018 A1 | 3/2017 | Perricone |
| 2017/0080020 A1 | 3/2017 | Perricone |
| 2017/0080021 A1 | 3/2017 | Perricone |
| 2017/0106014 A1 | 4/2017 | Perricone |
| 2017/0136059 A1 | 5/2017 | Perricone |

FOREIGN PATENT DOCUMENTS

| | | |
|---|---|---|
| EP | 0 482 554 A2 | 4/1992 |
| EP | 0 561 330 A1 | 9/1993 |
| EP | 0 722 323 A1 | 7/1996 |
| EP | 0 727 323 A1 | 8/1996 |
| EP | 1 323 436 A1 | 7/2003 |
| EP | 1 757 278 A1 | 2/2007 |
| EP | 2 685 962 | 1/2014 |
| JP | 60-058915 A | 4/1985 |
| JP | 60-155109 A | 8/1985 |
| JP | S63-502117 A | 8/1988 |
| JP | H05-502042 A | 4/1993 |
| JP | H05-51338 B2 | 8/1993 |
| JP | H06-316530 | 11/1994 |
| JP | 10-194994 A | 7/1998 |
| JP | 11-079975 | 3/1999 |
| JP | 2000-086501 | 3/2000 |
| JP | 2000-504033 A | 4/2000 |
| JP | 2000-509031 A1 | 7/2000 |
| JP | 2000-517311 | 12/2000 |
| JP | 2001-500886 A | 1/2001 |
| JP | 2001-507689 A | 6/2001 |
| JP | 2001-509136 | 7/2001 |
| JP | 2008-545714 | 12/2008 |
| JP | 2009-514792 | 4/2009 |
| JP | 2009-534298 | 9/2009 |
| WO | WO 1987/04592 A1 | 8/1987 |
| WO | WO 1992/03122 A1 | 3/1992 |
| WO | WO 1997/38579 A1 | 10/1997 |
| WO | WO 1998/13025 A1 | 4/1998 |
| WO | WO 1998/22090 A1 | 5/1998 |
| WO | WO 1999/056725 A1 | 11/1999 |
| WO | WO 2001/001963 A1 | 1/2001 |
| WO | WO 2001/049268 A1 | 7/2001 |
| WO | WO 2001/076537 A1 | 10/2001 |
| WO | WO 2002/064115 A1 | 8/2002 |
| WO | WO 2002/064166 A1 | 8/2002 |
| WO | WO 2003/101480 A1 | 12/2003 |
| WO | WO 2004/060314 A2 | 7/2004 |
| WO | WO 2004/060315 A2 | 7/2004 |
| WO | WO 2006/042701 A1 | 4/2006 |
| WO | WO 2006/100154 A1 | 9/2006 |
| WO | WO 2006/128121 A2 | 11/2006 |
| WO | WO 2007/106034 A1 | 9/2007 |
| WO | WO 2009/045481 A1 | 4/2009 |
| WO | WO 2009/114368 A2 | 9/2009 |
| WO | WO 2009/155689 A1 | 12/2009 |
| WO | WO 2010/129777 A1 | 11/2010 |
| WO | WO 2012/125214 A1 | 9/2012 |

OTHER PUBLICATIONS

U.S. Appl. No. 15/281,179, filed Sep. 30, 2016, Perricone.
U.S. Appl. No. 15/282,112, filed Sep. 30, 2016, Perricone.
U.S. Appl. No. 15/282,142, filed Sep. 30, 2016, Perricone.
U.S. Appl. No. 15/041,237, filed Feb. 11, 2016, Perricone.
U.S. Appl. No. 15/281,522, filed Sep. 30, 2016, Perricone.
U.S. Appl. No. 15/281,917, filed Sep. 30, 2016, Perricone.
U.S. Appl. No. 15/279,526, filed Sep. 30, 2016, Perricone.
U.S. Appl. No. 14/924,654, filed Oct. 27, 2015, Perricone.
U.S. Appl. No. 14/943,301, filed Nov. 17, 2015, Perricone.
EP 12712423.8, Mar. 2, 2015, European Office Action.
PCT/US2012/000151, Aug. 20, 2012, International Search Report and Written Opinion.
PCT/US2012/000151, Sep. 26, 2013, International Report on Patentability.
PCT/US2013/060348, Dec. 13, 2013, International Search Report and Written Opinion.
PCT/US2013/060348, Apr. 2, 2015, International Preliminary Report on Patentability.
PCT/US2013/060356, Mar. 4, 2014, International Search Report and Written Opinion.
PCT/US2013/060356, Apr. 2, 2015, International Preliminary Report on Patentability.
PCT/US2013/060362, Feb. 26, 2014, International Search Report and Written Opinion.
PCT/US2013/060362, Apr. 2, 2015, International Preliminary Report on Patentability.
PCT/US2013/060364, Feb. 5, 2014, Invitation to Pay Additional Fees.
PCT/US2013/060364, May 8, 2014, International Search Report and Written Opinion.
PCT/US2013/060364, Apr. 2, 2015, International Preliminary Report on Patentability.
PCT/US2013/060368, Feb. 25, 2014, International Search Report and Written Opinion.
PCT/US2013/060368, Apr. 2, 2015, International Preliminary Report on Patentability.
PCT/US2013/060374, Dec. 9, 2013, International Search Report and Written Opinion.
PCT/US2013/060374, Apr. 2, 2015, International Preliminary Report on Patentability.
PCT/US2013/060381, Mar. 6, 2014, International Search Report and Written Opinion.
PCT/US2013/060381, Apr. 2, 2015, International Preliminary Report on Patentability.
PCT/US2013/060386, Dec. 9, 2013, International Search Report and Written Opinion.
PCT/US2013/060386, Mar. 24, 2015, International Preliminary Report on Patentability.
PCT/US2013/060389, Dec. 9, 2013, International Search Report and Written Opinion.
PCT/US2013/060389, Apr. 2, 2015, International Preliminary Report on Patentability.
European Office Action dated Mar. 2, 2015 in connection with Application No. 12712423.8.
International Search Report and Written Opinion for Application No. PCT/US2012/000151 dated Aug. 20, 2012.
International Preliminary Report on Patentability for Application No. PCT/US2012/000151 dated Sep. 26, 2013.
International Search Report and Written Opinion for PCT/US2013/060348 dated Dec. 13, 2013.
International Preliminary Report on Patentability for Application No. PCT/US2013/060348 dated Apr. 2, 2015.
International Search Report and Written Opinion for Application No. PCT/US2013/060356 dated Mar. 4, 2014.
International Preliminary Report on Patentability for Application No. PCT/US2013/060356 dated Apr. 2, 2015.
International Search Report and Written Opinion for Application No. PCT/US2013/060362 dated Feb. 26, 2014.
International Preliminary Report on Patentability for Application No. PCT/US2013/060362 dated Apr. 2, 2015.

(56) References Cited

OTHER PUBLICATIONS

Invitation to Pay Additional Fees for Application No. PCT/US2013/060364 dated Feb. 5, 2014.
International Search Report and Written Opinion for Application No. PCT/US2013/060364 dated May 8, 2014.
International Preliminary Report on Patentability for Application No. PCT/US2013/060364 dated Apr. 2, 2015.
International Search Report and Written Opinion for Application No. PCT/US2013/060368 dated Feb. 25, 2014.
International Preliminary Report on Patentability for Application No. PCT/US2013/060368 dated Apr. 2, 2015.
International Search Report and Written Opinion for Application No. PCT/US2013/060374 dated Dec. 9, 2013.
International Preliminary Report on Patentability for Application No. PCT/US2013/060374 dated Apr. 2, 2015.
International Search Report and Written Opinion for Application No. PCT/US2013/060381 dated Mar. 6, 2014.
International Preliminary Report on Patentability for Application No. PCT/US2013/060381 dated Apr. 2, 2015.
International Search Report and Written Opinion for Application No. PCT/US2013/060386 dated Dec. 9, 2013.
International Preliminary Report on Patentability for Application No. PCT/US2013/060386 dated Apr. 2, 2015.
International Search Report and Written Opinion for Application No. PCT/US2013/060389 dated Dec. 9, 2013.
International Preliminary Report on Patentability for Application No. PCT/US2013/060389 dated Apr. 2, 2015.
[No Author Listed] About Soy Phospholipids. American Lecithin Company. Copyright 2000-2003. Last accessed online via http://www.americanlecithin.com/aboutphos.html on Sep. 29, 2007. 2 pages. (The year of publication is sufficiently earlier than the effective U.S. filing date and any foreign priority date so that the particular month of publication is not in issue. See MPEP 609.04(a)).
[No Author Listed] Database WPI, Week 201304; Thomson Scientific, London, GB; AN 2013-A79457. XP002725745.
[No Author Listed] Dow Corning MSDS Dow corning 200 fluid 5 cst. Material Safety Data Sheet. Version 1.3. Revision date Apr. 21, 2008. 8 pages.
[No Author Listed] Dow Corning Product Information: 200® Fluid Fluid 50cs, 100cs, 200cs, 350cs, 500cs, 1000cs. Ref. No. 25-991B-01. Dated Oct. 11, 2000. 4 pages.
[No Author Listed] Dow Corning. Information About Low Viscosity Silicone Fluids: 200® Fluid, 5cs; 200® Fluid, 10cs; 200® Fluid, 20cs. Product Information Sheet. Form No. 25-941-97. 1997.(The year of publication is sufficiently earlier than the effective U.S. filing date and any foreign priority date so that the particular month of publication is not in issue. See MPEP 609.04(a)) 2 pages.
[No Author Listed] Dow Corning® 190 Fluid Product Data Sheet. Dow Corning 190 Fluid is a silicone glycol coplolymer. Last accessed on Sep. 18, 2006 <https://www.dowcorning.com/applications/search/default.aspx?R=66EN> 1 page.
[No Author Listed] Dow Corning® 190 Fluid. INCI Name: PEG/PPG-18/18 Dimethicone. Production Information Sheet. Ref No. 22-1616C-01. Dated May 17, 2002. 4 pages.
[No Author Listed] Dow Corning® 190 Fluid. Material Safety Data Sheet. Version 1.6. Revision date Sep. 19, 2005. 7 pages.
[No Author Listed] Dow Corning® 190 Fluid. Textile, Leather & Non-woven. Silicone-ethylene oxide/propylene oxide copolymer. 3 pages. Mar. 3, 2005.
[No Author Listed] Frequently Asked Questions: How long can I store liposomes? Avanti Polar Lipids, Inc. Last accessed on Jun. 13, 2007. <http://avantilipids.com/DisplayFAQ.asp?Q=3> 1 page.
[No Author Listed] Frequently Asked Questions: How should I store my liposomes? Avanti Polar Lipids, Inc. Last accessed on Jun. 13, 2007. <http://avantilipids.com/DisplayFAQ.asp?Q=1> 1 page.
[No Author Listed] Frequently Asked Questions: What are the differences between liposomes and micelles? Avanti Polar Lipids, Inc. Last accessed on Jun. 13, 2007. <http://avantilipids.com/DisplayFAQ.asp?Q=4> 1 page.

[No Author Listed] Frequently Asked Questions: What is an SUV and LUV and how do they differ? Avanti Polar Lipids, Inc. Last accessed on Jun. 13, 2007. <http://avantilipids.com/DisplayFAQ.asp?Q=22> 1 page.
[No Author Listed] Google Search Results for "polyenylphosphatidylcholine phosphatidylcholi". Searched Sep. 29, 2007. 2 pages.
[No Author Listed] Liposome. Wikipedia. Last accessed on Jun. 11, 2007. <http://en.wikipedia.org/wiki/Liposome> 3 pages.
[No Author Listed] Liquid Crystal. Wikipedia. Last accessed on Jun. 22, 2009. <http://en.wikipedia.org/wiki/Liquid_crystal> 13 pages.
[No Author Listed] Oxytocin. Wikipedia. Last accessed on May 4, 2011. <http://en.wikipedia.org/wiki/Oxytocin> 16 pages.
[No Author Listed] Phosal 50 PG MSDA. 2007. 3 pages.
[No Author Listed] Phosal® 50 PG data sheet. Sep. 10, 2007; 1 page.
[No Author Listed] Phosphatidylcholine. (Monograph). Alternative Medicine Review. Apr. 1, 2002. last accessed online via http://www.encyclopedia.com/doc/1G1-85522987.html on Sep. 29, 2007. 9 pages.
[No Author Listed] Phospholipon® 80. Technical Data. American Lecithin Company. Copyright 2001-2011.
[No Author Listed] Preparations of liposomes. Avanti Polar Lipids, Inc. Last accessed on Jun. 13, 2007. <http://www.avantilipids.com/PreparationOfLiposomes.html> 3 pages.
Agarwal et al., Preparation and In Vitro Evaluation of Miconazole Nitrate-Loaded Topical Liposomes. Pharmaceutical Technology. Nov. 2002, p. 48-60.
Ahn et al., Phase properties of liquid-crystalline Phosphatidylcholine/Phosphatidylethanolamine bilayers revealed by fluorescent probes. Arch Biochem Biophys. Sep. 15, 1999;369(2):288-94.
Anderson, A Role for Nitric Oxide in Muscle Repair: Nitric Oxide-mediated Activation of Muscle Satellite Cells. Molecular Biology of the Cell. May 2000;11:1859-74.
Barenholz et al., Handbook of nonmedical applications of liposomes. 1996;3:217.
Benson et al, "Optimization of Drug Delivery 4. Transdermal Drug Delivery," Aus J Hosp Pharm, 27(6): 441-448 (1997).
Bergenstahl et al., Phase equilibria in the system soybean lecithin/water. Progress in Colloid & Polymer Science. 1983;68:48-52. (The year of publication is sufficiently earlier than the effective U.S. filing date and any foreign priority date so that the particular month of publication is not in issue. See MPEP 609.04(a)).
Bhattacharjee, "More Than the Patch: New Ways to Take Medicine Via Skin," New York Times, Jul. 2, 2002, p. F5.
Bonavida et al., Novel therapeutic applications of nitric oxide donors in cancer: roles in chemo- and immunosensitization to apoptosis and inhibition of metastases. Nitric Oxide. Sep. 2008;19(2):152-7. Epub Apr. 24, 2008.
Brandl et al., Morphology of semisolid aqueous phosphatidylcholine dispersions, a freeze fracture electron microscopy study. Chemistry and Physics of Lipids. May 30, 1997;87(1):65-72.
Brannon-Peppas, Polymers in Controlled Drug Delivery. Medical Plastics and Biomaterials Magazine. Nov. 1997:34-44.
Brisby et al., Nitric Oxide as a Mediator of Nucleus Pulposus-induced Effects on Spinal Nerve Roots. J Orthop Res. 2000;18(5):815-20.
Brunelli et al., Nitric oxide release combined with nonsteroidal antiinflammatory activity prevents muscular dystrophy pathology and enhances stem cell therapy. Proc Natl Acad Sci U S A. Jan. 2, 2007;104(1):264-9. Epub Dec. 20, 2006.
Calabrese et al., Nitric oxide in the central nervous system: neuroprotection versus neurotoxicity. Nature Rev Neurosci. Oct. 2007;8:766-75.
Cevc et al. "Ultraflexible Vesicles, Transfersomes, Have an Extremely Low Pore Penetration Resistance and Transport Therapeutic Amounts of Insulin Across the Intact Mammalian Skin." Biochem. et Biophys. Acta 1998, 1368, 201-215.
Cevc, Transdermal Drug Carriers: Basic Properties, Optimization and Transfer Efficiency in the Case of Epicutaneously Applied Peptides, Journal of Controlled Release 36: 3-16 (1995).

(56) References Cited

OTHER PUBLICATIONS

Chapman, Phase transitions and fluidity characteristics of lipids and cell membranes. Q Rev Biophys. May 1975;8(2):185-235.

Chetty et al., Novel Methods of Insulin Delivery: An Update, Critical Reviews in Therapeutic Drug Carrier Systems, 15(6): 629-670 (1998).

Christie, Phosphatidylcholine and Related Lipids, www.lipid.co.uk, May 5, 2003. 3 pages.

Cole et al., Challenges and opportunities in the encapsulation of liquid and semi-solid formulations into capsules for oral administration. Adv Drug Deliv Rev. Mar. 17, 2008;60(6):747-56. Epub Nov. 9, 2007.

Corswant et al., Triglyceride-based microemulsion for intravenous administration of sparingly soluble substances. J Pharm Sci. Feb. 1998;87(2):200-8.

Cox, Roundup's inert surfactant is poisonous. Journal of Pesticide Reform. 1988 Spring;8(1):30.

Daddona, Recent Advances in Peptide, Protein and Macromolecule Drug Delivery, Current Opinion in Drug Discovery & Development, 2(2): 168-171 (1999).

Daniels, "Galenic Principles of Modern Skin Care Products," Skin Care Forum, Issue 25, Apr. 2001.

Dong, Modern and Practical New Dosage forms and New Technique of Traditional Chinese Medicine. People's Medical Publishing House, 1st Edition. Apr. 2001;307-308.

Duong et al. Intracellular nitric oxide delivery from stable NO-polymeric nanoparticle carriers. Chem Commun. 2013; 49:4190-4192.

Engels et al., Liquid crystalline surfactant phases in chemical applications. J Mater Chem. 1998;8(6):1313-20. (The year of publication is sufficiently earlier than the effective U.S. filing date and any foreign priority date so that the particular month of publication is not in issue. See MPEP 609.04(a)).

Esposito, Elisabette et al., "Lipid-Based Supramolecular Systems for Topical Application: A Preformulatory Study," Published(Italy) Nov. 18, 2003, 15 pages. AAPS PharmSci 2003; 5 (4) Article 30 (http://aapspharmsci.org).

Filippin et al., Nitric oxide and repair of skeletal muscle injury. Nitric Oxide. Nov.-Dec. 2009;21(3-4):157-63. doi: 10.1016/j.niox.2009.08.002. Epub Aug. 12, 2009.

Gad, Pharmaceutical Manufacturing Handbook: Production and Processes. John Wiley & Sons, Inc. New Jersey. 2008:1344.

Greydanus et al. Acne vulgaris and chronically ill adolescents. International Journal on Disability and Human Development. Jul. 2008; 7(3):319-327.

Guo et al, "Transdermal Delivery of Insulin in Mice by Using Lecithin Vesicles as a Carrier," Drug Delivery, 7:113-116 (2000).

Huang et al., Nitric oxide-loaded echogenic liposomes for nitric oxide delivery and inhibition of intimal hyperplasia. J Am Coll Cardiol. Aug. 11, 2009;54(7):652-9.

Imbert et al., Measuring the encapsulation of cosmetic ingredients into liposomes: A method for large, hydrophilic compounds. J Soc Cosmet Chem. Nov./Dec. 1996;47(6):337-49.

Kaminski et al., Nitric oxide: biologic effects on muscle and role in muscle diseases. Neuromuscul Disord. Sep. 2001;11(6-7):517-24.

King et al., Transdermal delivery of insulin from a novel biphasic lipid system in diabetic rats. Diabetes Technol Ther. 2002;4(4):479-88.

Kirsten et al., Polyenylphosphatidylcholine improves the lipoprotein profile in diabetic patients. International Journal of Clinical Pharmacology and Therapeutics. 1994;32(2):53-6. (The year of publication is sufficiently earlier than the effective U.S. filing date and any foreign priority date so that the particular month of publication is not in issue. See MPEP 609.04(a)).

Lawrence et al., Microemulsion-based media as novel drug delivery systems. Adv Drug Deliv Rev. Dec. 6, 2000;45(1):89-121.

Luo, Theory and Practice of Modern Physical Pharmacy. Shanghai Scientific and Technological Literature Press, 1st Edition. Apr. 2005;337-338.

Maeda et al., Preparation of poly(L-lactic acid)-polysiloxane-calcium carbonate hybrid membranes for guided bone regeneration. Biomaterials. Mar. 2006;27(8):1216-22. Epub Sep. 6, 2005.

Maurer et al., Developments in liposomal drug delivery systems. Expert Opin Biol Ther. Nov. 2001;1(6):923-47.

Maurer et al., Developments in liposomal drug delivery systems. Expert Opin Biol Ther. 2001;1(6):1-25.

Miller et al., Recent developments in nitric oxide donor drugs. Br J Pharmacol. Jun. 2007;151(3):305-21. Epub Apr. 2, 2007.

Miller et al., Gaseous nitric oxide bactericidal activity retained during intermittent high-dose short duration exposure. Nitric Oxide. Feb. 2009;20(1):16-23.

Mitragotri, "Synergistic Effect of Enhancers for Transdermal Drug Delivery," Pharmaceutical Research, 17(11):1354-1359 (2000).

Moller et al., Direct measurement of nitric oxide and oxygen partitioning into liposomes and low density lipoprotein. J Biol Chem. Mar. 11, 2005;280(10):8850-4. Epub Jan. 4, 2005.

Mueller-Goymann, Liquid crystals in drug delivery. Encylcopedia of Pharmaceutical Technology. 1988-2000;20:117-46. (The year of publication is sufficiently earlier than the effective U.S. filing date and any foreign priority date so that the particular month of publication is not in issue. See MPEP 609.04(a)).

Namkoong et al., Therapeutic Application of Nitric Oxide in Human Diseases. Biomolecules & Therapeutics. Oct. 31, 2010;18(4):351-62.

O'Donnell et al., Nitration of unsaturated fatty acids by nitric oxide-derived reactive species. Methods Enzymol. 1999;301:454-70.

Patki et al., "Progress Made in Non-Invasive Insulin Delivery," Indian Journal of Pharmacology, 28:143-151 (1996).

Prescott, Methods in Cell Biology. Academic Press. 1976. Chapter 4. p. 34, 4 pages.

Qi et al., Interactions of insulin with dipalmitoylphosphatidylcholine liposomes. Acta Pharma Sinica. Dec. 2000;35(12):924-8. Chinese.

Rawat et al., Lipid carriers: a versatile delivery vehicle for proteins and peptides. Yakugaku Zasshi. Feb. 2008;128(2):269-80.

Robin, a physiological handbook for teachers of yogasana. 2002:283-5.

Scholfield, Composition of soybean lecithin. J Am Oil Chem Soc. 1981;58(1):889-92.

Seabra et al., Topically applied S-nitrosothiol-containing hydrogels as experimental and pharmacological nitric oxide donors in human skin. Br J Dermatol. Nov. 2004;151(5):977-83.

Shah et al., Cubic phase gels as drug delivery systems. Adv Drug Deliv Rev. Apr. 25, 2001;47(2-3):229-50.

Shahidi, Nutraceutical and Specialty Lipids and their Co-Products. CRC Press. Mar. 2006 14:515.

Shekhter et al., Beneficial effect of gaseous nitric oxide on the healing of skin wounds. Nitric Oxide. Jun. 2005;12(4):210-9.

Sjoblom, Emulsions: A fundamental and practical approach. Proc of the NATO Advanced Research Workshop on Emulsions. Emulsions. 1992:189.

Stojanovic et al. Endogenous estrogens increase postischemic hyperemia in the skin microcirculation. Journal of Cardiovascular Pharmacology. May 5, 2005; 45(5):414-417.

Subczynski et al., Permeability of nitric oxide through lipid bilayer membranes. Free Radic Res. May 1996;24(5):343-9.

Tiefenbacher et al., Endothelial dysfunction of coronary resistance arteries is improved by tetrahydrobiopterin in atherosclerosis. Circulation. Oct. 31, 2000;102(18):2172-9.

Trehan et al., "Recent Approaches in Insulin Delivery," Drug Development and Industrial Pharmacy, 24(7): 589-97 (1998).

Tyle, Liquid crystals and their applications in drug delivery. Controlled Release of Drugs: Polymers and Aggregate Systems. Chapter 4. Morton Rosoff Ed., VCH Publishers New York, NY. 1989, pp. 125-162.

Valenta et al., Evaluation of novel soya-lecithin formulations for dermal use containing ketoprofen as a model drug. J Control Release. Jan. 3, 2000;63(1-2):165-73.

Vasa et al., Nitric oxide activates telomerase and delays endothelial cell senescence. Circ Res. 2000;87:540-542.

(56) References Cited

OTHER PUBLICATIONS

Weiner et al. "Liposome-Collagen Gel Matrix: A Novel Sustained Drug Delivery System." J. Pharm. Sci. 1985, 74(9), 922-5.

Wimalawansa et al., Can We Use the Nitric Oxide Donor, Nitroglycerine for Prevention of Postmenopausal Bone Loss? Bone. Pergamon Press. May 1, 2009;44:S91.

Wimalawansa, Nitric Oxide and Bone. Annals NY Acad Sci. Apr. 1, 2010;1192(1):391-403.

Xie et al., Therapy of cancer metastasis by activation of the inducible nitric oxide synthase. Cancer Metastasis Rev. Mar. 1998;17(1):55-75.

Yoon et al. Estrogen dermatitis responding to leuprolide acetate [2]. Journal of Dermatology. May 5, 2005; 32(5):405-406.

Yuen et al., Treatment of chronic painful diabetic neuropathy with isosorbide dinitrate spray: a double-blind placebo-controlled crossover study. Diabetes Care. Oct. 2002;25(10):1699-703.

* cited by examiner

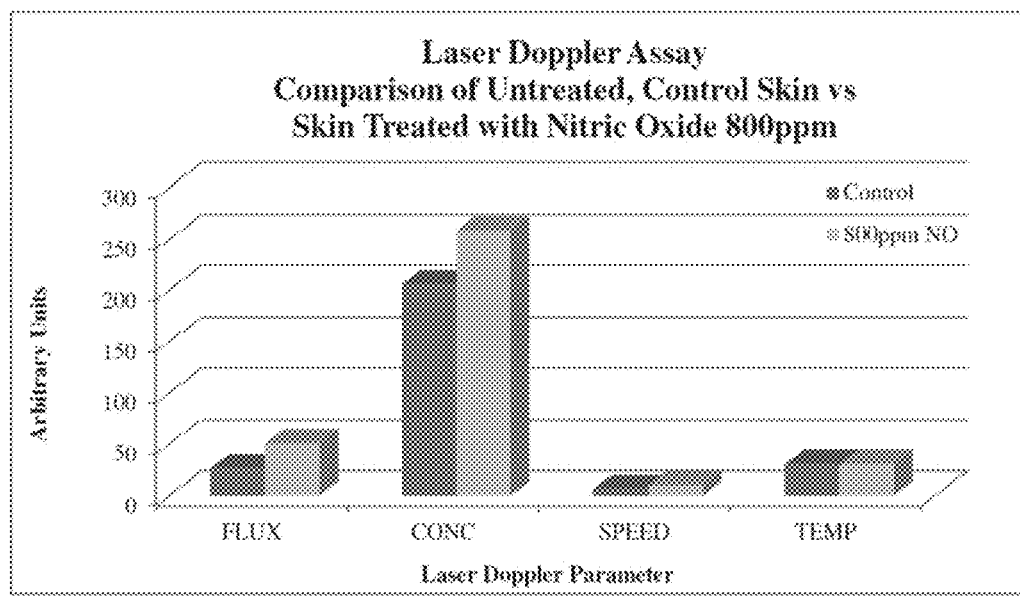

TECHNIQUES AND SYSTEMS FOR TREATMENT OF NEUROPATHIC PAIN AND OTHER INDICATIONS

RELATED APPLICATIONS

This application is a continuation of U.S. patent application Ser. No. 14/924,651, filed Oct. 27, 2015, entitled "Techniques and Systems for Treatment of Neuropathic Pain and Other Indications," by Nicholas V. Perricone, which is a continuation of U.S. patent application Ser. No. 14/492,279, filed Sep. 22, 2014, entitled "Techniques and Systems for Treatment of Neuropathic Pain and Other Indications," by Nicholas V. Perricone, which is a continuation of U.S. patent application Ser. No. 13/801,313, filed Mar. 13, 2013, entitled "Techniques and Systems for Treatment of Neuropathic Pain and Other Indications," by Nicholas V. Perricone, which is a continuation-in-part of U.S. patent application Ser. No. 13/623,027, filed Sep. 19, 2012, entitled "Techniques and Systems for Treatment of Neuropathic Pain and Other Indications," by Nicholas V. Perricone, each of which is incorporated herein by reference in its entirety.

FIELD

The present invention generally relates to compositions and methods for transdermal drug delivery, including treatment of neuropathic pain and other conditions.

BACKGROUND

Neuropathic pain is a form of chronic pain and can be classified as peripheral or central. Peripheral neuropathic pain is caused by injury or infection of peripheral sensory nerves, whereas central neuropathic pain is caused by damage to the CNS or/and the spinal cord. Both peripheral and central neuropathic pain can occur without obvious initial nerve damage. The clinical causes of neuropathic pain are widespread and include both trauma and disease. Various metabolic diseases may be the cause of neuropathic changes and may subsequently be implicated in neuropathic pain. An example of such a neuropathy is diabetic neuropathy, which occurs in a large number of patients suffering from diabetes and may be associated with a large number of clinical symptoms such as a feeling of numbness, tingling sensation, or pain. Neuropathic pain may also result from cancer, either from nerve damage directly caused by the cancer (e.g., compression by a tumor), or as a side effect of chemotherapy, radiation or surgery.

SUMMARY

The present invention generally relates to compositions and methods for transdermal drug delivery, including treatment of neuropathic pain and other conditions. The subject matter of the present invention involves, in some cases, interrelated products, alternative solutions to a particular problem, and/or a plurality of different uses of one or more systems and/or articles.

In one aspect, provided herein is a method comprising administering, to the skin of a subject having or at risk of neuropathic pain, a composition comprising an effective amount of nitric oxide and a carrier having a phosphatidylcholine component entrapping the nitric oxide.

In another aspect, provided herein is a method comprising contacting the skin of a subject having or at risk of neuropathic pain with a composition comprising an emulsion comprising a first phase comprising nitric oxide and lecithin, and a second phase comprising an emulsifier, wherein the lecithin is present at least about 0.25% by weight of the composition, and wherein the first phase comprises no more than about 250 ppm of water by weight of the composition. In certain embodiments, the compositions is applied to the skin of the subject at a location where treatment of neuropathic pain is desired.

Several methods are disclosed herein of administering a subject with a compound for prevention or treatment of a particular condition. It is to be understood that in each such aspect of the invention, the invention specifically includes, also, the compound for use in the treatment or prevention of that particular condition, as well as use of the compound for the manufacture of a medicament for the treatment or prevention of that particular condition.

In another aspect, the present invention encompasses methods of making one or more of the embodiments described herein, for example, a composition comprising nitric oxide. In still another aspect, the present invention encompasses methods of using one or more of the embodiments described herein, for example, a composition comprising nitric oxide.

Other advantages and novel features of the present invention will become apparent from the following detailed description of various non-limiting embodiments of the invention. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWING

The FIGURE shows results from the laser Doppler assay in four human study participants.

DETAILED DESCRIPTION

The present invention generally relates to compositions and methods for treatment of subjects having or at risk of neuropathic pain or other conditions. In some cases, the composition may include nitric oxide. The nitric oxide may be present within a first phase comprising a lecithin, such as phosphatidylcholine. In certain embodiments, the lecithin is present in liposomes, micelles, or other vesicles containing nitric oxide. The composition can take the form of a gel, a cream, a lotion, an ointment, a solution, a solid "stick," etc., that can be rubbed or sprayed onto the skin, e.g., onto a location with neuropathic pain, or on another suitable portion of the skin. Other aspects of the present invention are generally directed to methods of making or using such compositions, methods of promoting such compositions, kits including such compositions, or the like.

According to one aspect of the present invention, a composition as described herein is used to treat neuropathic pain or other conditions. To "treat" a disorder means to reduce or eliminate a sign or symptom of the disorder, to stabilize the disorder, and/or to reduce or slow further progression of the disorder. Thus, in one set of embodiments, the application of nitric oxide, e.g., in a nitric oxide-containing matrix, to the skin may result in clinical improvement. In some cases, the delivery of nitric oxide to the skin, e.g., to the epidermis and/or dermis, may be achieved at a controlled rate and/or concentration. Without wishing to be bound by any theory, it is believed that impaired nitric oxide generation is involved in the pathogenesis of neuropathic pain, e.g., diabetic neuropathic pain (see, e.g., Yuen et al., Diabetes Care 2002, 25:1699-1703). Also, the vasodilation effects of nitric oxide may induce angiogenesis of the vasa nervorum, increasing the analgesic effect of nitric oxide on neuropathic pain.

In some embodiments, the nitric oxide in the composition is stable at room temperature, and may remain active for extended periods of time, e.g., at least 1 year, at least 1.5 years, at least 2 years, at least 2.5 years, at least 3 years, at least 4 years, etc. The nitric oxide may be released, for example, when the composition is exposed to an aqueous environment, e.g., within the body. Without wishing to be bound by any theory, it is believed that when the composition is applied to the skin, the liquid crystal structure collapses, delivering nitric oxide to a desired area of treatment. The concentration of the nitric oxide inside the liquid crystal matrix can be varied in terms of concentration. The matrix also may act as a sustained release and delivery system in some embodiments. It is also believed that the liquid crystal is highly penetrating, such that nitric oxide can be delivered to the epidermis, dermis and dermal vascular for systemic release as well as to subcutaneous fat, at least under some conditions.

Thus, in one set of embodiments, application of nitric oxide, e.g., in a penetrating matrix gel delivering the active nitric oxide, may act as a preventative of and/or be used to treat neuropathic pain. In another set of embodiments, a composition as described herein is applied to the skin of a subject, e.g., one having or at risk of neuropathic pain. For instance, in some embodiments, a composition as is described herein is contacted with the skin of a subject at a location where treatment of neuropathic pain is desired. Exemplary types of neuropathic pain that may be treated by compositions described herein include postherpetic neuralgia, HIV-distal sensory polyneuropathyl, diabetic neuropathic pain, neuropathic pain associated with traumatic nerve injury, neuropathic pain associated with stroke, neuropathic pain associated with multiple sclerosis, neuropathic pain associated with syringomyelia, neuropathic pain associated with epilepsy, neuropathic pain associated with spinal cord injury, and neuropathic pain associated with cancer.

In some cases, the subject may be one that already has neuropathic pain. However, in other cases, the subject may not necessarily have neuropathic pain, but may be one that is at risk of developing neuropathic pain. For instance, the subject may be one has cancer or diabetes or has suffered a nerve injury.

In accordance with some embodiments of the invention, nitric oxide gas itself may be entrapped or contained within various compositions as discussed herein, for example, in liquid crystal multilamellar phosphatidylcholine. In addition, in certain embodiments as discussed below, the composition may be stable and can be stored for periods of time with little or no loss or reaction of the nitric oxide contained therein.

Since nitric oxide is an unstable and reactive gas, entrapment, storage, and release of nitric oxide requires careful formulation in some embodiments of the invention. For example, nitric oxide readily reacts with water to form nitrous acid ($HNO_2$), and thus, certain embodiments of the invention include compositions or phases that are substantially free of water. As another example, in one set of embodiments, nitric oxide may be contained within a first phase comprising a lecithin such as phosphatidylcholine, which may be present within a second phase comprising an emulsifier, such as is discussed herein. Other components, for example, transdermal penetration enhancers, adjuvants, surfactants, lubricants, etc. can also be present in certain cases.

Thus, the compositions of the invention comprise, in certain aspects, a phase comprising phosphatidylcholine and/or other lecithins in which nitric oxide is contained within or "trapped." The phosphatidylcholine or lecithin may be contained within a second phase, for example, comprising an emulsifier, which may cause the phosphatidylcholine or lecithin to form vesicles, e.g., micelles or liposomes. The phosphatidylcholine or lecithin composition can be unilamellar or multilamellar in some embodiments. In some instances, the presence of the second phase causes the phosphatidylcholine or lecithin to form a liquid crystal arrangement.

The nitric oxide is typically gaseous, and may be present within the composition as small bubbles and/or bound to lecithins or phosphatidylcholines within the composition. For example, the nitric oxide may be bound to double bonds present in the lecithins or phosphatidylcholines. Phosphatidylcholine is believed to stabilize and/or contain the nitric oxide. In some cases, stability of the composition can be achieved at room temperature (about 25° C.), and/or at other temperatures such as those described herein. Without wishing to be bound by any theory, it is believed that the phosphatidylcholine adopts a liquid crystal structure under such conditions, which can thereby contain the nitric oxide, e.g., as small gaseous bubbles, and/or through binding with lecithins or phosphatidylcholines.

Nitric oxide is typically reactive with water (e.g., forming nitrous acid), which contributes to its relatively short lifetime within the body or within other aqueous environments. Accordingly, in certain embodiments of the invention, the composition, or at least a phase of the composition comprising the nitric oxide (and/or the second phase, and/or one or more materials used to prepare a nitric oxide composition, and/or a nitric oxide composition prepared as described herein), is substantially free of water, e.g., comprising no more than about 10 wt %, no more than about 3 wt %, no more than about 1 wt %, no more than about 0.3 wt %, or no more than about 0.1 wt % water (i.e., relative to the weight of the overall composition). The composition may also have no more than about 1,000 ppm, no more than about 750 ppm, no more than about 500 ppm, no more than about 400 ppm, no more than about 300 ppm, no more than about 250 ppm, no more than about 200 ppm, no more than about 150 ppm, no more than about 100 ppm, no more than about 50 ppm, no more than about 25 ppm, or no more than about 10 ppm of water. In certain embodiments, no detectable water may be present in the composition, or at least within a phase of the composition comprising the nitric oxide. Any suitable technique can be used for determining the amount of water present in the composition, for example, Karl-Fisher titration. In some cases, the composition may also be free of any liquids that typically contain water, e.g., physiological buffers, body fluids, saline, or the like.

Any suitable amount of nitric oxide may be present within a composition prepared as described herein. For example, at least about 0.3 wt %, at least about 0.5 wt %, at least about 0.7 wt %, at least about 1 wt %, at least about 1.5 wt %, at least about 2 wt %, at least about 2.5 wt %, at least about 3 wt %, at least about 5 wt % at least about 10 wt %, at least about 20 wt %, at least about 30 wt %, at least about 40 wt %, at least about 50 wt %, at least about 60 wt %, at least about 70 wt %, at least about 80 wt %, at least about 90 wt %, at least about 100 wt %, at least about 110 wt %, or at least about 120 wt % of the composition can be nitric oxide, where the basis of the weight percentage is the weight of the composition before nitric oxide is added. For example, the nitric oxide may be present at between 70 wt % and about 120 wt % of the composition. In some embodiments, the nitric oxide may be present at a concentration of at least about 400 mg/kg, at least about 450 mg/kg, at least about 500 mg/kg, at least about 550 mg/kg, at least about 570 mg/kg, at least about 600 mg/kg, at least about 650 mg/kg, at least about 700 mg/kg, at least about 750 mg/kg, at least about 800 mg/kg, at least about 850 mg/kg, at least about 950 mg/kg, or at least about 1000 mg/kg of the composition. In certain cases, the nitric oxide may be present at a concentration of no more than about 2000 mg/kg, no more than about 1500 mg/kg, no more than about 1000 mg/kg, no more than about 960 mg/kg, no more than about 900 mg/kg, no more than about 800 mg/kg, no more than about 700 mg/kg, or no more than about 600 mg/kg. For example, the nitric oxide may be present at a concentration of between about 570 mg/kg and about 960 mg/kg.

In some embodiments, the nitric oxide is present at a concentration (e.g., on a per-mass basis) of at least about 100 ppm, at least about 200 ppm, at least about 300 ppm, at least about 400 ppm, at least about 500 ppm, at least about 600 ppm, at least about 700 ppm, at least about 800 ppm, at least about 900 ppm, at least about 1000 ppm, at least about 1100 ppm, at least about 1200 ppm, at least about 1300 ppm, at least about 1400 ppm, at least about 1500 ppm, at least about 1600 ppm, at least about 1700 ppm, at least about 1800 ppm, at least about 1900 ppm, at least about 2000 ppm, at least about 2500 ppm, at least about 3000 ppm, at least about 3500 ppm, at least about 4000 ppm, at least about 4500 ppm, at least about 5000 ppm, at least about 6000 ppm, at least about 7000 ppm, at least about 8000 ppm, at least about 9000 ppm, or at least about 10000 ppm of the composition. In other embodiments, the nitric oxide is present at a concentration of no more than about 11000 ppm, no more than about 10000 ppm, no more than about 9000 ppm, no more than about 8000 ppm, no more than about 7000 ppm, no more than about 6000 ppm, no more than about 5000 ppm, no more than about 4500 ppm, no more than about 4000 ppm, no more than about 3500 ppm, no more than about 3000 ppm, no more than about 2500 ppm, no more than about 2000 ppm, no more than about 1900 ppm, no more than about 1800 ppm, no more than about 1700 ppm, no more than about 1600 ppm, no more than about 1500 ppm, no more than about 1400 ppm, no more than about 1300 ppm, no more than about 1200 ppm, no more than about 1100 ppm, no more than about 1000 ppm, no more than about 900 ppm, no more than about 800 ppm, no more than about 700 ppm, no more than about 600 ppm, no more than about 500 ppm, no more than about 400 ppm, or no more than about 300 ppm of the composition. For example, in some embodiments, nitric oxide is present at a concentration of between about 400 and about 900 ppm. NO content can be measured by any suitable technique. For example, in some embodiments, NO content is measured using a nitric oxide biosensor (e.g., nitric oxide macrosensor with nitric oxide specific electrode from WPI Instruments). In some embodiments, NO content is measured by a change in weight in the composition after adding NO.

In some embodiments, nitric oxide is present within a first phase comprising a lecithin, such as phosphatidylcholine. Phosphatidylcholine (herein abbreviated "PC") is a basic component of cell membrane bilayers and the main phospholipid circulating in the plasma of blood. Phosphatidylcholine typically has a phospholipid structure with a choline head group and a glycerophosphoric acid tail group. The tail group can be saturated or unsaturated. More than one tail group may be present in the phosphatidylcholine in some cases, and the tail groups may be the same or different. Specific non-limiting examples of phosphatidylcholines that could be used include one or a mixture of stearic, palmitic, margaric, and/or oleic acid diglycerides linked to a choline ester head group.

Phosphatidylcholines are a member of a class of compounds called lecithins. Typically, a lecithin is a composed of phosphoric acid, choline, fatty acids, glycerol, glycolipids, triglycerides, and/or phospholipids. In some cases, other lecithins may be used, in addition to or instead of a phosphatidylcholine. Non-limiting examples of other lecithins include phosphatidylethanolamine, phosphatidylinositol, or phosphatidic acid. Many commercial lecithin products are available, such as, for example, Lecithol®, Vitellin®, Kelecin®, and Granulestin®. Lecithin is widely used in the food industry. In some embodiments, certain compositions of the invention can contain synthetic or natural lecithin, or mixtures thereof. Natural preparations are used in some cases because they exhibit desirable physical characteristics, and/or may be economical or nontoxic. However, in other embodiments, non-natural preparations are used, or the composition can include both natural and non-natural preparations.

Any suitable amount of phosphatidylcholine or lecithin may be present within the composition. For example, at least about 0.25 wt %, at least about 0.5 wt %, at least about 1 wt %, at least about 2 wt %, at least about 3 wt %, at least about 5 wt %, at least about 8 wt %, at least about 10 wt %, at least about 20 wt %, at least about 30 wt %, at least about 40 wt %, at least about 50 wt %, at least about 60 wt %, at least about 70 wt %, at least about 80 wt %, or at least about 90 wt % of the entire composition can be a phosphatidylcholine or a lecithin. In some cases, the phosphatidylcholine or lecithin may be present at a concentration of no more than about 95 wt %, no more than about 90 wt %, no more than about 80 wt %, no more than about 70 wt %, no more than about 65 wt %, no more than about 60 wt %, no more than about 50 wt %, no more than about 40 wt %, no more than about 30 wt %, no more than about 20 wt %, or no more than about 10%. For instance, the phosphatidylcholine or lecithin may be present at between about 8 wt % and about 65 wt %, or between about 0 wt % and about 10 wt %, etc. One or more than one type of phosphatidylcholine or lecithin may be present.

Some delivery compositions of the present invention may contain polyenylphosphatidylcholine (herein abbreviated "PPC"). In some cases, PPC can be used to enhance epidermal penetration. The term "polyenylphosphatidylcholine," as used herein, means any phosphatidylcholine bearing two fatty acid moieties, wherein at least one of the two fatty acids is an unsaturated fatty acid with at least two double bonds in its structure, such as linoleic acid.

Certain types of soybean lecithin and soybean fractions, for example, can contain higher levels of polyenylphosphatidylcholine, with dilinoleoylphosphatidylcholine (18:2-18:2 phosphatidylcholine) as the most abundant phosphatidylcholine species therein, than conventional food grade lecithin. Such lecithins may be useful in formulating certain delivery compositions. In some embodiments, conventional soybean lecithin may be enriched with polyenylphosphatidylcholine, for instance, by adding soybean extracts containing high levels of polyenylphosphatidylcholine. As used herein, this type of phosphatidylcholine is called "polyenylphosphatidylcholine-enriched" phosphatidylcholine (herein-after referred to as PPC-enriched phosphatidylcholine), even where the term encompasses lecithin obtained from natural sources exhibiting polyenylphosphatidylcholine levels higher than ordinary soybean varieties. These products are commercially available, for example, from American Lecithin Company, Rhone-Poulenc and other lecithin vendors. American Lecithin Company markets its products with a "U" designation, indicating high levels of unsaturation; Rhone-Poulenc's product is a soybean extract containing about 42% dilinoleoylphosphatidylcholine and about 24% palmitoyllinoleylphosphatidylcholine (16:0 to 18:2 of PC) as the major phosphatidylcholine components. Another example of a suitable polyenylphosphatidylcholine is NAT 8729 (also commercially available from vendors such as Rhone-Poulenc and American Lecithin Company).

Any suitable amount of polyenylphosphatidylcholine may be present within the composition. For example, at least about 0.25 wt %, at least about 0.5 wt %, at least about 1 wt %, at least about 2 wt %, at least about 3 wt %, at least about 5 wt %, at least about 8 wt %, at least about 10 wt %, at least about 20 wt %, at least about 30 wt %, at least about 40 wt %, at least about 50 wt %, at least about 60 wt %, at least about 70 wt %, at least about 80 wt %, or at least about 90 wt % of the composition can be polyenylphosphatidylcholine. In some cases, the polyenylphosphatidylcholine may be present at a concentration of no more than about 95 wt %, no more than about 90 wt %, no more than about 80 wt %, no more than about 70 wt %, no more than about 65 wt %, no more than about 60 wt %, no more than about 50 wt %, no more than about 40 wt %, no more than about 30 wt %, no more than about 20 wt %, or no more than about 10%. For instance, the polyenylphosphatidylcholine may be present at between about 8 wt % and about 65 wt %. In some embodiments, at least about 20 wt %, at least about 30 wt %, at least about 40 wt %, at least about 50 wt %, at least about 60 wt %, at least about 70 wt %, at least about 80 wt %, at least about 90 wt %, or about 100 wt % of all of the phosphatidylcholine or lecithin in the composition is polyenylphosphatidylcholine.

While not wishing to be bound by any theory, it is believed that the PPC-enriched phosphatidylcholine forms a bilayer enveloping nitric oxide (and in some embodiments, other adjunct ingredients, if present) to create the drug delivery composition. The PPC-enriched phosphatidylcholine is believed to contribute to the stability of the nitric oxide, for example, by shielding the nitric oxide from water, and/or by enhancing its penetration into the skin or other area, e.g., a mucosal surface.

The first phase also comprises, in some embodiments of the invention, a fatty acid ester. Non-limiting examples include ascorbate palmitate or isopropyl palmitate. In some cases, the fatty acid ester is used as a preservative or an antioxidant. The composition can include any suitable amount of fatty acid ester, for example, at least about 1 wt %, at least about 3 wt %, at least about 5 wt %, at least about 10 wt %, at least about 20 wt %, at least about 30 wt %, at least about 40 wt %, at least about 50 wt %, etc. In some cases, no more than about 60 wt %, no more than about 50 wt %, no more than about 40 wt %, no more than about 30 wt %, no more than about 20 wt %, no more than about 18 wt %, no more than about 15 wt %, no more than about 12 wt %, or no more than about 10 wt % of the composition is fatty acid ester. For example, the composition may be between about 0 wt % and about 10 wt % fatty acid ester. The composition may include one or more than one fatty acid ester.

In certain embodiments, a drug delivery composition such as those described herein can be formulated to include a second phase. Typically, the second phase is substantially immiscible with the first phase comprising phosphatidylcholine or lecithin. Two phases that are substantially immiscible are able to form discrete phases when exposed to each other at ambient conditions (e.g., 25° C. and 1 atm) for extended periods of time (e.g., at least about a day). The phases can be separate identifiable phases (e.g., one may float above the other), or in some cases, the phases are intermingled, e.g., as in an emulsion. The stability of the discrete phases may be kinetic and/or thermodynamic in nature, in various embodiments.

In one set of embodiments, the second phase may comprise an emulsifier which causes the first phase comprising phosphatidylcholine or lecithin to form a liquid crystal, and/or vesicles such as micelles or liposomes. Typically, in a liquid crystal phase, vesicular structures such as micelles, liposomes, hexagonal phases, or lipid bilayers can be formed. In some cases, multilamellar structures may be present within the liquid crystal phase, although in other cases, only unilamellar structures may be present. For example, in certain cases, the PPC-enriched phosphatidylcholine can be loosely arranged in a multilamellar fashion, with nitric oxide and optional adjunct ingredients being bonded or otherwise entrapped or contained within the lipid bilayers formed therein. In some cases, the first phase (e.g., comprising PPC-enriched phosphatidylcholine) and the second phase can form a structure such as is disclosed in U.S. Pat. No. 7,182,956 to Perricone, et al. This is believed (without wishing to be bound by any theory) to form a loosely arranged, yet stable, PPC-enriched phosphatidylcholine-drug complex that may allow penetration and delivery of nitric oxide and optional adjunct ingredients to the skin, e.g., to the dermal vasculature.

In one set of embodiments, the second phase comprises an emulsifier. The emulsifier, in one embodiment, is a substance that is able to stabilize an emulsion by increasing its kinetic stability. The emulsifier may also be chosen in some cases to be relatively inert or non-toxic relative to the skin.

In some embodiments, the second phase may comprise a polyglycol. The polyglycol may include a polyhydric alcohol of a monomeric glycol such as polyethylene glycol (PEG) and/or polypropylene glycol (PPG). For example, the PEG or PPG may be PEG or PPG 200, 300, 400, 600, 1,000, 1,450, 3,350, 4,000, 6,000, 8,000, and 20,000, where the number indicates the approximate average molecular weight of the PEG or PPG. As is understood by those of ordinary skill in the art, a polyglycol composition often will comprise a range of molecular weights, although the approximate average molecular weight is used to identify the type polyglycol. More than one PEG and/or PPG can also be present in certain instances.

The second phase may comprise a surfactant in some embodiments. Non-limiting examples of surfactants include a siloxylated polyether comprising dimethyl, methyl(propylpolyethylene oxide propylene oxide, acetate) siloxane commercially available from vendors such as Dow Corning (Dow Corning 190 surfactant). Other examples of materials that can be used as (or within) the second phase include, but are not limited to, 1,2-propanediol, or silicone fluids containing low viscosity polydimethylsiloxane polymers, methylparaben (p-hydroxy benzoic acid methyl ester) commercially available from vendors such as Dow Corning (Dow Corning 200 silicone fluid). Still other examples include various siloxane or silicone compounds, e.g., hexamethyldisiloxane, amodimethicone, phenyltrimethicone, etc.

Additionally, purified water may be added to the second phase in some embodiments, although in other cases, little or no water is present in the second phase. For example, the first phase, the second phase, can contain less than 10%, less than 5%, less than 2%, less than 1%, or less that 0.05% (e.g., wt %) of water relative to the weight of the respective phase or of the entire composition. In some cases, the second phase may also comprise adjunct ingredients such as those described herein.

The second phase may include any one, or more than one, of the materials described above. In addition, any suitable amount of second phase can be used in accordance with various embodiments of the invention. For example, the second phase may be present at at least about 10 wt %, at least about 20 wt %, at least about 30 wt %, at least about 40 wt %, at least about 50 wt %, at least about 60 wt %, at least about 70 wt %, at least about 80 wt %, or at least about 90 wt % of the composition. In some cases, the ratio of the first phase (e.g., comprising phosphatidylcholine or lecithin) to the second phase can be at least about 1:3, at least about 1:2, at least about 1:1, at least about 2:1, at least about 3:1, or at least about 4:1, etc.

In another set of embodiments, the composition may also include one or more transdermal penetration enhancers. Examples of transdermal penetration enhancers include, but are not limited to, 1,3-dimethyl-2-imidazolidinone or 1,2-propanediol. Other examples include cationic, anionic, or nonionic surfactants (e.g., sodium dodecyl sulfate, polyoxamers, etc.); fatty acids and alcohols (e.g., ethanol, oleic acid, lauric acid, liposomes, etc.); anticholinergic agents (e.g., benzilonium bromide, oxyphenonium bromide); alkanones (e.g., n-heptane); amides (e.g., urea, N,N-dimethyl-m-toluamide); organic acids (e.g., citric acid); sulfoxides (e.g., dimethylsulfoxide); terpenes (e.g., cyclohexene); ureas; sugars; carbohydrates or other agents. The transdermal penetration enhancers can be present in any suitable amount within the composition. For example, at least about 10 wt %, at least about 20 wt %, at least about 30 wt %, at least about 40 wt %, or at least about 50 wt % of the composition may comprise one or more transdermal penetration enhancers. In some cases, no more than about 60 wt %, no more than about 50 wt %, no more than about 40 wt %, no more than about 30 wt %, no more than about 20 wt %, no more than about 10 wt %, no more than about 9 wt %, or no more than about 5 wt % of the composition comprises transdermal penetration enhancers. For example, the composition may have between about 0 wt % and about 5 wt % of one or more transdermal penetration enhancers.

In other embodiments, the composition may be modified in order to control depth of penetration. For example, in certain embodiments, the composition includes one or more polymers that act to reduce penetration depth of nitric oxide. Controlled depth of penetration may be important for indications where local administration is desired without systemic effects. Examples of transdermal penetration barrier polymers include, but are not limited to, silicone waxes, acrylate polymers, and dimethicone copolymers. In certain embodiments, a transdermal penetration barrier polymer is nonionic. A transdermal penetration barrier polymer can be present in any suitable amount within the composition. For example, at least about 10 wt %, at least about 20 wt %, at least about 30 wt %, at least about 40 wt %, or at least about 50 wt % of the composition may comprise one or more transdermal penetration barrier polymers. In some cases, no more than about 60 wt %, no more than about 50 wt %, no more than about 40 wt %, no more than about 30 wt %, no more than about 20 wt %, no more than about 10 wt %, no more than about 9 wt %, or no more than about 5 wt % of the composition comprises a transdermal penetration barrier polymer. For example, the composition may have between about 0 wt % and about 5 wt % of one or more transdermal penetration barrier polymers.

As a specific non-limiting example of one set of embodiments, a polyenylphosphatidylcholine comprises a certain material with the trade name NAT 8729, and optionally at least one polyglycol (polyhydric alcohol of a monomeric glycol such as polyethylene glycol 200, 300, 400, 600, 1,000, 1,450, 3,350, 4,000, 6,000, 8,000 and 20,000). The composition can also comprise a PPC-enriched phosphatidylcholine material that is present within the first or second phase, e.g., comprising nitric oxide. The second phase may also comprise a surfactant such as a siloxylated polyether comprising dimethyl, methyl(propylpolyethylene oxide propylene oxide, acetate) siloxane commercially available from vendors such as Dow Corning (Dow Corning 190 surfactant) and lubricant such as silicone fluids containing low viscosity polydimethylsiloxane polymers, methylparaben (p-hydroxy benzoic acid methyl ester) commercially available from vendors such as Dow Corning (Dow Corning 200 silicone fluid).

In some embodiments, various compositions of the invention are formulated to be substantially clear or substantially transparent. Transparency may be useful, for instance, for product acceptance in the marketplace, e.g., when applied to the skin of a subject. However, in other embodiments, the composition is not necessarily transparent. Certain substances can be useful in providing a substantially transparent composition, for example, fatty acid esters such as ascorbate palmitate or isopropyl palmitate. In one set of embodiments, the composition may be substantially transparent such that incident visible light (e.g., have wavelengths of between about 400 nm and about 700 nm) can be transmitted through 1 cm of the composition with a loss in intensity of no more than about 50%, about 60%, about 70%, about 80%, or about 90% relative to the incident light. In some embodiments, there may be no substantial difference in the wavelengths that are absorbed by the composition (i.e., white light passing through the composition appears white), although in other cases, there can be more absorption at various wavelengths (for example, such that white light passing through the composition may appear colored).

Other components may also be present within the composition, in accordance with certain embodiments of the invention. For example, the composition may include volatile organic fluids, fatty acids, volatile aromatic cyclic compounds, high molecular weight hydrocarbons, or the like.

In accordance with certain aspects of the invention, the composition may be prepared by mixing a first phase and a second phase together, then passing nitric oxide through the mixture. As discussed above, the second phase can comprise an emulsifier, or any other components discussed herein. The first phase may comprise a lecithin such as phosphatidylcholine and/or polyenylphosphatidylcholine, e.g., PPC-enriched phosphatidylcholine, for instance, as described herein. In some embodiments, other components are also mixed into the composition, before or after (or while) adding nitric oxide, for example, transdermal penetration enhancers, adjuvants, polyglycols (e.g., PEG and/or PPG), surfactants, lubricants, etc. as discussed herein. In some embodiments, however, nitric oxide may be passed through the first phase prior to mixing of the first phase with the second phase.

In one set of embodiments, after forming the mixture, nitric oxide can be passed into or through the mixture, for example, by blowing bubbles of nitric oxide through the mixture. Nitric oxide may be delivered into the mixture under pressures such as between about 3,000 Pa and about 15,000 Pa, between about 5,000 Pa and about 10,000 Pa, or between about 6,000 Pa and about 8,000 Pa, and/or temperatures such as between about 0° C. and about 50° C., between about 20° C. and about 35° C., or about 25° C. and about 30° C. However, higher or lower pressures also may be used in some embodiments as aspects of the invention are not limited in this respect.

In certain embodiments, the nitric oxide is bubbled through the mixture until the mixture begins to at least partially solidify. As an example, the viscosity of the mixture may increase to at least about 1,000 cP, at least about 2,000 cP, at least about 3,000 cP, at least about 5,000 cP, at least about 7,000 cP, at least about 10,000 cP, at least about 12,000 cP, at least about 15,000 cP, at least about 20,000 cP, at least about 30,000 cP, at least about 40,000 cP, at least about 50,000 cP, at least about 60,000 cP, at least about 70,000 cP, or at least about 80,000 cP. The nitric oxide can be passed through the mixture as pure nitric oxide, and/or with other gases (e.g., a noble gas, for example, argon). In some cases, a nitric oxide donor may be passed into the mixture, and therein, at least some of the nitric oxide donor can be converted into nitric oxide. In other embodiments, however, the final composition may have lower viscosities, for example, such that the composition is liquid, or could be sprayed onto the skin.

In one set of embodiments, the nitric oxide can be bubbled through the mixture to cause the viscosity of the mixture to increase. For example, the viscosity can increase until the mixture begins to form a gel, a cream, a lotion, an ointment, a solid "stick," or the like. A cream may be, for example, a semi-solid emulsion, e.g., comprising a first phase and a second phase. The first phase may be discontinuous (e.g., comprising small droplets or vesicles, such as is discussed herein) and the second phase may be continuous, or vice versa. In some cases, however, both the first phase and the second phase are co-continuous within the mixture.

In some embodiments of the invention, a composition may be prepared as discussed above, then diluted, e.g., with a diluent, to produce a final composition. For example, a "stock" composition may be initially prepared, e.g., having a relatively high nitric oxide concentration, then the stock composition diluted to produce a final composition, e.g., before use, before storage, before packaging, etc. In some embodiments, the diluent used may be a component as discussed herein (for example, forming at least a portion of the second phase), and the same or different materials than may be present in the initial composition may be used. The dilution ratio (amount of diluent added, relative to the initial composition) may be at least about 2, at least about 3, at least about 5, at least about 10, at least about 15, at least about 20, at least about 25, at least about 30, at least about 50, or at least about 100, or any other suitable factor.

A composition may be prepared and/or stored at any suitable temperature and under any suitable conditions. In some embodiments, for instance, a composition can be prepared and/or stored under limited or no oxygen conditions, as oxygen can adversely react with nitric oxide. The composition can also be prepared and/or stored under limited or no nitrogen and/or carbon dioxide, as both can also react adversely with nitric oxide. For instance, the composition may be prepared and/or stored in a sealed environment (e.g., stored in a sealed container). The sealed environment (e.g., container) can be at least substantially devoid of gas, and/or contains a gaseous mixture that excludes, or at least is depleted in, oxygen. In some embodiments, an environment depleted in oxygen may have less than about 20%, less than about 15%, less than about 10%, less than about 5%, about 1% or less, about 0.1% or less, about 0.01% or less, about 0.001% or less, oxygen (e.g., as a wt % or as molar % per volume). For example, the gaseous mixture may include a noble gas, such as argon, helium, neon, etc. In one set of embodiments, the container may comprise a multi-layered metallic and/or polymeric barrier, e.g., formed from Glaminate® (American Can Company). For instance, the container may have the shape of a tube. Thus, in certain embodiments, the container is substantially resistant to oxygen permeation, nitrogen permeation, and/or carbon dioxide permeation. In certain embodiments, the container is substantially watertight, for example, such that substantially no water is absorbed by the container, or such that no water is able to pass through the container even if the container is filled with water.

As previously discussed, nitric oxide can react with water, and thus, compositions described herein may be prepared and/or stored under conditions where substantially no water is present. For example, nitric oxide and/or a nitric oxide containing preparation described herein may be prepared and/or stored under relatively low relative humidities (e.g., less than about 50% RH, less than about 40% RH, less than about 30% RH, less than about 20% RH, or less than about 10% RH), and/or in the presence of a suitable desiccant, such as phosphorous pentoxide or silica gel.

In certain embodiments, the mixture may be mixed with or otherwise include adjunct ingredients, if applicable, and nitric oxide may be introduced to the mixture, e.g., bubbles of nitric oxide gas may be blown into the mixture until the mixture hardens to obtain the desired final composition. As a specific non-limiting example, a nitric oxide composition may be formed by preparing a non-liposome multilamellar liquid crystal phosphatidylcholine phase, for example, by providing a polyglycol, then introducing phosphatidyl choline into the glycol at room temperature to form a phosphatidylcholine solution. The phosphatidylcholine often comes as a solid (e.g., as a "brick" of material), and the phosphatidylcholine may be broken down into smaller pieces to aid in mixing, e.g., by "shaving" or grinding the phosphatidylcholine solid. The phosphatidylcholine solution is mixed until the phosphatidylcholine solution is substantially clear, then one may warm the phosphatidylcholine solution to 40° C., mill the warmed solution (i.e., low agitation after the initial mixing), combine siloxylated polyether and polydimethylsiloxane to form a fluid, add the fluid to the warmed solution and milling until the solution is clear, adding methyl paraben or other suitable lubricant to the solution and milling until the methyl paraben dissolves in the solution, warm water to 40° C. and adding the warmed water slowly to the solution, and then ceasing milling of the solution and "sweeping" the solution (e.g., with a sweep mixer) to cool to room temperature. Nitric oxide gas can then be bubbled or otherwise introduced into the solution while cooling the solution until the solution begins to harden or becomes stiff, e.g., having the consistency of a gel or a cream, such as previously described. In some cases, the resulting composition is sealed in a container, for example, as discussed herein. Any suitable container may be used, e.g., a tube or a bottle. In addition, the composition (e.g., within the container) may be stored at room temperature, or any other suitable temperature. For example, a composition of the invention may be stored at or below 80° C., e.g., at or below room temperature (about 25° C.) or in a refrigerator (e.g., at 4° C.) for extended period of storage, for instance, to prevent nitric oxide leakage or denaturing. In some cases, storage may extend for at least about a week, at least about 4 weeks, at least about 6 months, at least about a year, etc.

It is surprising that, according to some embodiments, nitric oxide not only can be entrapped in phosphatidylcholine or lecithin compositions such as those described herein, but also that such entrapped compositions may have a long shelf life, especially when refrigerated. No loss or reaction of nitric oxide is expected during extended refrigerated storage, at least under certain conditions. For instance, in certain embodiments, the composition may be stored at temperatures of less than about 80° C., less than about 70° C., less than about 60° C., less than about 50° C., less than about 40° C., less than about 30° C., less than about 25° C., less than about 20° C., less than about 15° C., less than about 10° C., less than about 5° C., less than about 0° C., etc., for extended periods of time, e.g., at least about a day, at least about a week, at least about 4 weeks, at least about 6 months, etc.

Without wishing to be bound by theory, it is believed that nitric oxide forms reversible physical bonds, similar to hydrogen bonds or van der Waals forces, with phosphatidylcholine or other lecithin molecules, e.g., containing one or more double bonds, which may allow nitric oxide to become entrapped and thereby remain intact for an extended period of time, e.g., during storage. These physical bonds, however, are believed to be not very stable, and may in some cases be easily broken up, for example, upon various physical agitations such as rubbing the composition against the skin, thereby releasing the entrapped nitric oxide. While others have stabilized other substances or drugs within phosphatidylcholine or lecithin compositions or vesicles, for example, protein drugs such as insulin, it is surprising that a small, highly reactive molecule such as NO could similarly be stabilized, especially when it would have been expected that a molecule as small as NO would readily diffuse away from such compositions and/or would have reacted with water that is typically present within such compositions.

In some embodiments, it is believed that other species reactive with water could also be similarly stabilized, e.g., within a composition as herein described. Any species that ordinarily reacts with water could be stabilized within such compositions. Examples of such species include, but are not limited to, lithium, or drugs or polymers with labile bonds susceptible to hydrolysis, for instance, certain peptides, polysaccharides, polylactic acid, polyglycolic acid, etc.

In certain aspects of the invention, a composition such as those described herein can be administered to a subject, such as a human subject, by rubbing it on the skin of the subject, e.g., in areas located at or at least within the vicinity of a desired target area. Without wishing to be bound by any theory, it is believed that phosphatidylcholine provides or facilitates delivery of nitric oxide to the skin, allowing nitric oxide to be delivered to a target area. In some embodiments, the composition can be applied, by rubbing the composition topically against the skin, which allows the composition (or at least, nitric oxide) to be absorbed by the skin. The composition can be applied once, or more than once. For example, the composition may be administered at predetermined intervals. In some embodiments, for instance, the composition may be applied once per day, twice per day, 3 times per day, 4 times per day, once every other day, once every three days, once every four days, etc. The amount of nitric oxide necessary to bring about the therapeutic treatment is not fixed per se, and may depend upon factors such as the desired outcome, the type and severity the disease or condition, the form of nitric oxide, the concentration of nitric oxide present within the composition, etc.

Thus, another aspect of the invention provides methods of administering any composition such as discussed herein to a subject. The compositions of the invention may be applied to a subject for local or systemic delivery, depending on the application. The compositions of the invention may also be applied to any suitable area of the skin. For example, the compositions may be applied to the upper chest or arms, or to any hairy or non-hairy portion of the skin, e.g., to promote systemic delivery of nitric oxide, or the composition may be applied locally, e.g., at an area of the skin where treatment is desired.

When administered, the compositions of the invention are applied in a therapeutically effective, pharmaceutically acceptable amount as a pharmaceutically acceptable formulation. Any of the compositions of the present invention may be administered to the subject in a therapeutically effective dose. When administered to a subject, effective amounts will depend on the particular condition being treated and the desired outcome. A therapeutically effective dose may be determined by those of ordinary skill in the art, for instance, employing factors such as those described herein and using no more than routine experimentation.

In some embodiments, an effective amount is an amount sufficient to have a measurable positive effect on blood flow and/or vasodilation, and/or a measurable negative effect on blood pressure. In some embodiments, the effect on blood flow and/or vasodilation is observed local to the site of topical application. In some embodiments, an effective amount is an amount sufficient to have a measurable effect on neuropathic pain as evidenced by an appropriate clinical parameter, e.g., change in average daily pain score, change in intensity of dynamic allodynia, change in intensity of static hyperalgesia, change in pain quality on the Short-Form McGill Pain Questionnaire, change in Galer Neuropathic Pain Scale, change in Patient Global Impression of Change relative to baseline, change in total Profile of Mood States score, change in Sleep Interference Scale). In some embodiments, an effective amount is an amount sufficient to obtain a systemic level of nitric oxide that is sufficient to have a desired effect, e.g., have a measurable positive effect on blood flow and/or vasodilation, have a measurable negative effect on blood pressure, and/or have a measurable effect on neuropathic pain as evidenced by an appropriate clinical parameter.

The compositions described herein can be used in combination therapy with one or more additional therapeutic agents. For combination treatment with more than one active agent, where the active agents are in separate dosage formulations, the active agents may be administered separately or in conjunction. In addition, the administration of one element may be prior to, concurrent to, or subsequent to the administration of the other agent. In certain embodiments, the additional therapeutic agent is present in a provided composition in addition to nitric oxide. In other embodiments, the additional therapeutic agent is administered separately from the nitric oxide containing composition.

When co-administered with other agents, an "effective amount" of the second agent will depend on the type of drug used. Suitable dosages are known for approved agents and can be adjusted by the skilled artisan according to the condition of the subject, the type of condition(s) being treated and the amount of a compound described herein being used. In cases where no amount is expressly noted, an effective amount should be assumed. For example, compounds described herein can be administered to a subject in a dosage range from between about 0.01 to about 10,000 mg/kg body weight/day, about 0.01 to about 5000 mg/kg body weight/day, about 0.01 to about 3000 mg/kg body weight/day, about 0.01 to about 1000 mg/kg body weight/day, about 0.01 to about 500 mg/kg body weight/day, about 0.01 to about 300 mg/kg body weight/day, about 0.01 to about 100 mg/kg body weight/day.

In one set of embodiments, the dosage may be between about 0.01 mg and about 500 g, between about 0.01 mg and about 300 g, between about 0.01 mg and about 100 g, between about 0.01 mg and about 30 g, between about 0.01 mg and about 10 g, between about 0.01 mg and about 3 g, between about 0.01 mg and about 1 g, between about 0.01 mg and about 300 mg, between about 0.01 mg and about 100 mg, between about 0.01 mg and about 30 mg, between about 0.01 mg and about 10 mg, between about 0.01 mg and about 3 mg, between about 0.01 mg and about 1 mg, between about 0.01 mg and about 0.3 mg, or between about 0.01 mg and about 0.1 mg.

In certain embodiments, a nitric oxide containing composition as described herein, and the additional therapeutic agent are each administered in an effective amount (i.e., each in an amount which would be therapeutically effective if administered alone). In other embodiments, a nitric oxide containing composition as described herein, and the additional therapeutic agent are each administered in an amount which alone does not provide a therapeutic effect (a subtherapeutic dose). In yet other embodiments, a nitric oxide containing composition as described herein can be administered in an effective amount, while the additional therapeutic agent is administered in a sub-therapeutic dose. In still other embodiments, a nitric oxide containing composition as described herein can be administered in a subtherapeutic dose, while the additional therapeutic agent is administered in an effective amount.

As used herein, the terms "in combination" or "co-administration" can be used interchangeably to refer to the use of more than one therapy (e.g., one or more prophylactic and/or therapeutic agents). The use of the terms does not restrict the order in which therapies (e.g., prophylactic and/or therapeutic agents) are administered to a subject.

Co-administration encompasses administration of the first and second amounts of the compounds in an essentially simultaneous manner, such as in a single pharmaceutical composition, for example, capsule or tablet having a fixed ratio of first and second amounts, or in multiple, separate capsules or tablets for each. In addition, such co-administration also encompasses use of each compound in a sequential manner in either order. When co-administration involves the separate administration of the first amount of a composition as described herein, and a second amount of an additional therapeutic agent, the compounds are administered sufficiently close in time to have the desired therapeutic effect. For example, the period of time between each administration which can result in the desired therapeutic effect, can range from minutes to hours and can be determined taking into account the properties of each compound. For example, a composition as described herein, and the second therapeutic agent can be administered in any order within about 24 hours of each other, within about 16 hours of each other, within about 8 hours of each other, within about 4 hours of each other, within about 1 hour of each other or within about 30 minutes of each other.

More specifically, a first therapy (e.g., a prophylactic or therapeutic agent such as a composition described herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

Examples of therapeutic agents that may be combined with a composition of this disclosure, either administered separately or in the same pharmaceutical composition, include, but are not limited to, antidepressants (e.g., duloxetine, venlafaxine, milnacipran, amitriptyline, nortriptyline, desipramine, bupropion, klomipramine), anticonvulsants (e.g., pregabalin, gabapentin, carbamazepine, oxcarbazepine, lamotrigine), opioids (e.g., methadone, ketobemidone, morphine, oxycodone, buprenorfin, tramadol), local anesthetics (e.g., lidocaine, capsaicin), acetaminophen, NSAIDS and coxibs (e.g., celecoxib, etoricoxib, lumiracoxib, valdecoxib, parecoxib, diclofenac, loxoprofen, naproxen, ketoprofen, ibuprofen, nabumeton, meloxicam, piroxicam), botulinum toxin type A, NMDA antagonists (e.g., dextromethorphan, memantine, ketamine), dietary supplements (e.g., alpha lipoic acid, benfotiamine), and biologically active peptides (e.g., opioid peptides (e.g., endorphins, enkephalins, dynorphins), RAP-103, NGF peptide agonists, NCAM-mimetic peptides, chi-conopeptides). Compositions described herein may also be administered in conjunction with other therapies, such as spinal cord stimulators, implanted spinal pumps, motor cortex stimulation, and deep brain stimulation.

In certain embodiments of the invention, the administration of various compositions of the invention may be designed so as to result in sequential exposures to the composition over a certain time period, for example, hours, days, weeks, months, or years. This may be accomplished, for example, by repeated administrations of a composition of the invention by one or more of the methods described herein, or by a sustained or controlled release delivery system in which the composition is delivered over a prolonged period without repeated administrations. Administration of the composition using such a delivery system may be, for example, by a transdermal patch. Maintaining a substantially constant concentration of the composition may be preferred in some cases.

In one set of embodiments, a composition such as is discussed herein may be applied to the skin of a subject, e.g., at any suitable location. In some embodiments, the suitable location is at a site having neuropathic pain. In some embodiments, the suitable location is near a site having neuropathic pain (e.g., within 1-10, 10-30, 20-50 cm). In some embodiments, the suitable location is at a site on the skin that is above the neuropathic pain, i.e., site of pain does not necessarily have to be at the level of the skin. In some embodiments, the neuropathic pain can be below the skin, and the penetration depth of the formulation and/or amount added can be adjusted accordingly. In some embodiments, the suitable location is an area that covers the site of neuropathic pain and is, for example, about 1, 2, 3, 4, 5, 6, 7, 8, 9, 10, 15, 20, 25, 30, 40, or 50 cm in diameter. In some embodiments, when the composition is administered for systemic delivery, the suitable location can be anywhere on the body. The composition may be contacted using any suitable method. For example, the composition may be rubbed on, poured on, applied with an applicator (e.g., a gauze pad, a swab, a bandage, etc.), or the like. In some cases, the composition can be a liquid, a gel, a cream, a lotion, an ointment, a solid "stick," or the like, that can be applied to the skin by hand, for example, by rubbing or spraying.

In some embodiments, provided compositions are not used for treating erectile dysfunction or sexual dysfunction. In certain embodiments, a subject of the methods described herein does not suffer from erectile dysfunction or sexual dysfunction. In some embodiments, a provided composition is not applied to the skin of a subject on or near a male or female genital region to treat sexual dysfunction and/or to enhance sexual performance or experience. In some embodiments, a provided composition is not applied to the perineal region (e.g., penis), or to the vulva of a subject.

In some embodiments, provided compositions are not used to promote wound healing. In certain embodiments, a subject of the methods described herein does not suffer from a wound. In certain embodiments, a provided composition is not applied to a wound. Examples of wounds include cuts, scrapes, other traumatic wounds, burns or other accidental wounds, e.g., an anal fissure, a surgical site, a trauma site, a burn, an abrasion, a sunburn, a cut or laceration on the skin, or any other damaged region of the skin. In some embodiments, the composition is not applied to a mucosal surface of the subject, for example, to the nose. In certain embodiments, provided compositions are not used to treat wounds that result from surgical intervention (e.g., any medical intervention or operation that requires wound healing as part of the recovery process). In some embodiments, a composition of the invention is not used to prepare a tissue site for wound healing prior to the wound (e.g., prior to surgery) and/or after the wound (e.g., and/or after surgery). In some embodiments, a composition of the invention is not applied to the surface of a wound or to skin prior to a wound.

In some embodiments, a composition of the invention is not applied to a surgical device, tool, or other substrate, such as sutures, implants, surgical tools, surgical dressings, bandages, or other substrates that may come into contact with wounded tissue during surgery. In some embodiments, compositions of the invention may be provided as a cream or ointment as described in more detail herein.

In some embodiments, a composition of the present invention is not used to promote hair growth. In some embodiments, a provided composition is not applied in a region on a subject where hair loss is undesirable, such as the skin surface of the scalp. In some embodiments, a subject of methods provided herein is not a subject who is bald, balding, or has thinning hair or may be at risk of losing hair.

Compared to other means of administration, the use of topical administration in certain embodiments of the present invention has various advantages, including one or more of the following. In some cases, administration of a composition and delivery of nitric oxide as discussed herein is easier and more effective than other drug administration routes, for example, oral delivery. Unlike oral administration where a substantial amount of nitric oxide may be destroyed during the digestive process, nitric oxide delivered topically is not exposed to the digestive tract. Topical application may also allow, in some instances, relatively steady delivery of nitric oxide to the desired target area without the cyclic dosages typical of orally or parenterally administered drugs. In some embodiments, topical application may also avoid toxic side effects associated with sustained increased levels of nitric oxide typical of oral or parenteral administration.

Compared to other topical delivery systems that employ nitric oxide donors (an entity that is able to release nitric oxide, such as L-arginine, nitroglycerin, or amyl nitrite) as a nitric oxide source, various aspects of the present invention utilizing nitric oxide gas have several advantages, including one or more of the following. Nitric oxide can be released relatively quickly in some embodiments, because the release does not necessarily involve chemical transformations of nitric oxide donors to release nitric oxide. The concentration of nitric oxide can accumulate quickly upon topical administration, leading to good therapeutic effect in certain embodiments of the invention. In some embodiments, the release rate of nitric oxide can be controlled, for instance, by physical actions (e.g., by controlling how much of the composition is applied to the skin), in comparison to nitric oxide donors which release nitric oxide upon chemical stimulation. Moreover, certain embodiments of the present invention employ phosphatidylcholine, a component of cell membranes, as a carrier which improves the penetration and absorption of nitric oxide into cells and tissues. Thus, certain compositions of the present invention will be non-toxic or biocompatible.

The compositions of the present invention may additionally comprise one or more adjunct ingredients, for instance, pharmaceutical drugs, skin care agents, and/or excipients. For example, compositions of the invention may include additional ingredients such as salts, buffering agents, diluents, excipients, chelating agents, fillers, drying agents, antioxidants, antimicrobials, preservatives, binding agents, bulking agents, silicas, solubilizers, or stabilizers. Non-limiting examples include species such as calcium carbonate, sodium carbonate, lactose, kaolin, calcium phosphate, or sodium phosphate; granulating and disintegrating agents such as corn starch or algenic acid; binding agents such as starch, gelatin or acacia; lubricating agents such as magnesium stearate, stearic acid, or talc; time-delay materials such as glycerol monostearate or glycerol distearate; suspending agents such as sodium carboxymethylcellulose, methylcellulose, hydroxypropylmethylcellulose, sodium alginate, polyvinylpyrrolidone; dispersing or wetting agents such as lecithin or other naturally-occurring phosphatides; thickening agents such as cetyl alcohol or beeswax; buffering agents such as acetic acid and salts thereof, citric acid and salts thereof, boric acid and salts thereof, or phosphoric acid and salts thereof; or preservatives such as benzalkonium chloride, chlorobutanol, parabens, or thimerosal. Suitable concentrations can be determined by those of ordinary skill in the art, using no more than routine experimentation. Those of ordinary skill in the art will know of other suitable formulation ingredients, or will be able to ascertain such, using only routine experimentation.

Preparations can include sterile aqueous or nonaqueous solutions, suspensions and emulsions, which can be isotonic with the blood of the subject in certain embodiments. Examples of nonaqueous solvents are polypropylene glycol, polyethylene glycol, vegetable oil such as olive oil, sesame oil, coconut oil, arachis oil, peanut oil, mineral oil, organic esters such as ethyl oleate, or fixed oils including synthetic mono or di-glycerides. Aqueous solvents include water, alcoholic/aqueous solutions, emulsions or suspensions, including saline and buffered media. Parenteral vehicles include sodium chloride solution, 1,3-butandiol, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents and inert gases and the like. Those of skill in the art can readily determine the various parameters for preparing and formulating the compositions of the invention without resort to undue experimentation.

In one set of embodiments, the efficacy of various compositions of the invention as applied to a subject may be determined or monitored by studying the carotid arteries, which generally supply the head and neck with blood. For example, in certain embodiments, a composition of the invention may be applied to a subject for systemic delivery, and one effect of the nitric oxide may be to cause vasodilation. By studying the carotid artery, the effect of the nitric oxide delivery may be monitored, and if necessary, the dosing of nitric oxide adjusted. Any suitable method may be used to monitor the carotid artery, e.g., ultrasound, a carotid Doppler machine, functional MRI, PET scanning, etc. In other embodiments, if local delivery without systemic effects is desired, the carotid artery can be monitored for any systemic effects.

In one aspect, one or more compositions described herein may be formulated for oral delivery. In some embodiments, one or more compositions are provided in a capsule. A capsule can be a hard or soft water-soluble container, e.g., a gelatin container. Other examples of capsules include, but are not limited to polyglycolized glyceride, hydroxypropyl methylcellulose, Gelucire, iota carragennan, hydroxypropyl starch, polyvinyl alcohol, or the like, as well as combinations of these and/or other materials. In some cases, other materials may be added to the capsule shell, e.g., plasticizers, coloring agents, opacifiers, or the like. Examples of plasticizers include glycerin or sorbitol. A capsule can be coated to affect bioavailability and/or location of release. A capsule can be used to target release to gastric, duodenal, intestinal, or colonic locations within the gastro-intestinal tract of a subject. Upon release a composition can adhere to the gastric mucosa and delivery nitric oxide to the underlying tissue. In some embodiments, a composition described herein is mixed in a capsule with one or more fillers, diluents, glidants, or other agents. In some embodiments, a capsule wall is produced or coated to minimize oxygen and/or moisture penetration. In some embodiments, a composition is added to a capsule under low oxygen and/or low humidity conditions. In some embodiments, a capsule is stored under low oxygen and/or low humidity conditions. Other capsule materials may be found in, e.g. *Challenges and Opportunities in The Encapsulation of Liquid and Semi-Solid Formulations into Capsules for Oral Administration, Adv. Drug Deliv. Rev.,* 2008 Mar. 17; 60(6):747-756, incorporated by reference herein in its entirety.

In another aspect, the present invention is directed to a kit including one or more of the compositions discussed herein. A "kit," as used herein, typically defines a package or an assembly including one or more of the compositions of the invention, and/or other compositions associated with the invention, for example, as described herein. Each of the compositions of the kit may be provided in liquid form (e.g., in solution), or in solid form (e.g., a dried powder). In certain cases, some of the compositions may be constitutable or otherwise processable (e.g., to an active form), for example, by the addition of a suitable solvent or other species, which may or may not be provided with the kit. Examples of other compositions or components associated with the invention include, but are not limited to, solvents, surfactants, diluents, salts, buffers, chelating agents, fillers, antioxidants, binding agents, bulking agents, preservatives, drying agents, antimicrobials, needles, syringes, packaging materials, tubes, bottles, flasks, beakers, dishes, frits, filters, rings, clamps, wraps, patches, containers, and the like, for example, for using, administering, modifying, assembling, storing, packaging, preparing, mixing, diluting, and/or preserving the compositions components for a particular use, for example, to a sample and/or a subject.

A kit of the invention may, in some cases, include instructions in any form that are provided in connection with the compositions of the invention in such a manner that one of ordinary skill in the art would recognize that the instructions are to be associated with the compositions of the invention. For instance, the instructions may include instructions for the use, modification, mixing, diluting, preserving, administering, assembly, storage, packaging, and/or preparation of the composition and/or other compositions associated with the kit. In some cases, the instructions may also include instructions for the delivery and/or administration of the compositions, for example, for a particular use, e.g., to a sample and/or a subject. The instructions may be provided in any form recognizable by one of ordinary skill in the art as a suitable vehicle for containing such instructions, for example, written or published, verbal, audible (e.g., telephonic), digital, optical, visual (e.g., videotape, DVD, etc.) or electronic communications (including Internet or web-based communications), provided in any manner.

International Patent Application No. PCT/US2012/000151, filed Mar. 17, 2012, entitled "Topical Nitric Oxide Systems and Methods of Use Thereof," by Nicholas V. Perricone, et al., is incorporated herein by reference in its entirety. In addition, the following applications, filed on Sep. 19, 2012, each by Nicholas V. Perricone, are hereby incorporated by reference in their entireties: "Systems and Methods for Treatment of Acne Vulgaris and Other Conditions with a Topical Nitric Oxide Delivery System" (U.S. patent application Ser. No. 13/623,008); "Treatment of Skin and Soft Tissue Infection with Nitric Oxide" (U.S. patent application Ser. No. 13/623,010); "Methods and Systems for Treatment of Inflammatory Dermatoses with Nitric Oxide" (U.S. patent application Ser. No. 13/623,014); "Prevention and Treatment of Cardiovascular Diseases using Systems and Methods for Transdermal Nitric Oxide Delivery" (U.S. patent application Ser. No. 13/623,018); "Treatment and Prevention of Learning and Memory Disorders" (U.S. patent application Ser. No. 13/623,022); "Methods and Compositions for Muscular or Neuromuscular Diseases" (U.S. patent application Ser. No. 13/622,998); "Compositions and Methods for Treatment of Osteoporosis and Other Indications" (U.S. patent application Ser. No. 13/623,004); "Techniques and Systems for Treatment of Neuropathic Pain and Other Indications" (U.S. patent application Ser. No. 13/623,027); and "Cancer Treatments and Compositions for Use Thereof" (U.S. patent application Ser. No. 13/622,989).

The following examples are intended to illustrate certain embodiments of the present invention, but do not exemplify the full scope of the invention.

Example 1

This example illustrates one technique for preparing a composition in accordance with one embodiment of the invention. An accurate amount of a carrier (HNC 167-62) (see below) was introduced into a system. The carrier weight used in these experiments was approximately 250 g and the vessel size was 500 ml. The vessel was equipped with a mechanical stirrer, gas inlet, and gas outlet and was previously purged with argon for about an hour. The temperature of the carrier was kept at about 25-30° C. NO gas regulated at 5 psi (1 psi is about 6,900 Pa) and was then introduced at a controlled rate of about 1 bubble/s with continuous stirring. The color, consistency, and viscosity of the carrier did not appear to change if NO was bubbled for 30 minutes to 2 hours. After 6 hours, the weight of the carrier had increased by 0.15%, by 12 hours by 0.25%, and by 24 hours by 0.56%. These increases in weight were believed to be significant considering the relative small molecular weight of NO versus the carrier. Although there was a slight change in color during the experiment (the color changed to slightly more orange), IR spectrum analysis of the final product did not show any change versus the initial carrier, indicating no noticeable chemical change in the carrier. The carrier also can solidify upon cooling if the carrier is initially a solid at lower temperature. Accordingly, this example demonstrates that a composition containing NO can be prepared in accordance with one embodiment of the invention.

Example 2

In this example, six experiments were carried out to investigate the interaction of nitric oxide with three carriers (HNC 157-62, HNC 157-65, and HNC 157-69) as well as with 1,3-propanediol, using experimental conditions similar to that described for Example 1. In addition three experiments were performed to prepare carriers containing 800 ppm and 500 ppm nitric oxide. HNC 157-62 was formed of 65% Phospholipon-90G (American Lecithin Company), 18% isopropyl palmitate (Kraft Chemicals), 8% capric caprylic triglycerides (RITA Corp.), and 9% propanediol (Dupont). HNC 157-65 was formed of 65% Phospholipon-90G, 13% isopropyl palmitate, 14% capric caprylic triglycerides, 3% propanediol, and 5% dimethyl isosorbide (Croda). HNC 157-69 was formed from 65% Phospholipon-90G, 16% isopropyl palmitate, and 19% capric caprylic triglycerides.

The compositions were generally prepared as follows. Isopropyl palmitate, capric caprylic triglyceride, propanediol (for HNC 157-62 and HNC 157-65), and dimethyl isosorbide (for HNC 157-65) were mixed together and warmed to 40° C. Phospholipon-90G was then gradually added to this liquid mixture by mixing it. Phospholipon-90G is typically received as individual pellets, and is mixed into the solution until fully dissolved. The mixture was subsequently filtered through a sieve to remove any undissolved Phospholipon-90G.

Accordingly, the HNC carriers included 1,3-propanediol, Phospholipon-90G, isopropyl palmitate, capric and/or caporic triglycerides, and Arlasolve DMI (ICI America or Croda). Isopropyl palmitate, the capric and/or caporic triglycerides, and Arlasolve DMI are expected to be chemically inert towards nitric oxide, while the literature suggests that 1,2-propanediol and glycerol may be able to react with nitric oxide gas to form mononitrates. Accordingly, it would be expected that 1,3-propanediol may also react with NO to form mononitrates:

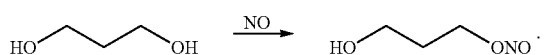

In addition, Phospholipon-90G is derived from soybean and contains esters of unsaturated fatty acids such as oleic, linoleic, and linolenic acids, and thus, the unsaturated fatty acid part of Phospholipon-90G would react with nitric oxide to lead to a variety of nitrated products.

Each carrier was taken in a 500 mL three necked flask equipped with a mechanical stirrer, gas inlet and a gas outlet. The system was purged with argon for one hour at room temperature (25° C.). Then nitric oxide gas was bubbled into the system. Then, nitric oxide gas was bubbled through carrier for stipulated amount of time. The changes in weight and color were noted. The details of individual experiments were as follows.

Experiment 1. The carrier was HNC 157-62. Nitric oxide gas was bubbled for 24 hours at 25° C. The initial weight of carrier was 168.53 g., and the final weight was 169.48 g. The net weight gained was 0.95 g and the percentage weight gain was 0.56%.

Experiment 2. The carrier used was HNC 157-62. Nitric oxide gas was bubbled for 48 hours at 25° C. The initial weight of carrier was 171.31 g., and the final weight was 174.21 g. The net weight gained was 2.90G and the percentage weight gain was 1.69%.

Experiment 3. In order to differentiate between chemical reaction vs. physical absorption, the above reaction mixtures were heated at 55-60° C. for four hours. Minimal loss of weight was observed (~200 mg), indicating no loss of absorbed nitric oxide gas. However, more intense orange color developed during this process, indicating some decomposition of the nitrites formed.

Experiment 4. The carrier used was HNC 157-65. Nitric oxide gas was bubbled for 24 hours at 25° C. The initial weight of carrier was 171.66 g., and the final weight was 172.98 g. The net weight gained was 1.32 g and percentage weight gain was 0.77%.

Experiment 5. The carrier used was HNC 157-69 (same as HNC 157-62, except it had no 1,3-propanediol). Nitric oxide gas was bubbled for 40 hours at 25° C. The initial weight of carrier was 171.02 g., and the final weight was 171.97 g. The net weight gained was 0.95 g and the percentage weight gain was 0.56%.

Experiment 6. Nitric oxide gas was bubbled through 1,3-propanediol (neat) for 40 hours at 25° C. The initial weight of the 1,3-propanediol was 178.81 g., and the final weight was 178.97 g. The net weight gained was 0.16 g and the percentage weight gain was 0.09%.

Experiment 7. For preparation of 800 ppm NO, the carrier used was HNC 157-62. Nitric oxide gas was bubbled for 2 hours at 25° C. The initial weight of carrier was 238.16 g., and the final weight was 238.35 g. The net weight gained was 0.19 g and the percentage weight gain 0.0798% (~800 ppm). See entry 5 in Table 1.

Experiment 8. For preparation of 500 ppm NO, the carrier used was HNC 157-65. Nitric oxide gas was bubbled for 2 hours at 25° C. The initial weight of carrier was 250.37 g., and the final weight was 250.50 g. The net weight gained was 0.13 g and the percentage weight gain was 0.0519% (~500 ppm). See entry 6 in Table 1.

Experiment 9. For preparation of 800 ppm NO, the carrier used was HNC 157-62. Nitric oxide gas was bubbled for 15 min at 25° C. The initial weight of carrier was 252.24 g., and the final weight was 252.45 g. The net weight gained was 0.21 g and the percentage weight gain 0.083% (~800 ppm).

These experiments were conducted with carriers the HNC 157-62, HNC 157-65, HNC 157-69, and 1,3-propanediol.

As described above and in Table 1, weight gains ranging from 0.5% to 1.7% were observed when nitric oxide gas was passed through the carriers. In order to determine the nature of interaction between nitric oxide and carrier, the carrier was heated after nitric oxide absorption at 60° C. for four hours. Practically no loss of weight was observed, which indicated that the nitric oxide gas reacted chemically with the carriers (entries 1-4 in Table 1).

In order to investigate the reactivity of 1,3-propanediol with nitric oxide, nitric oxide absorption was studied using (a) HNC 157-69, which did not contain 1,3-propanediol, and (b) 1,3-propanediol by itself. HNC 157-69 gained 0.95 g or 0.56% weight, much lower compared to its 1,3-propanediol containing analog HNC 157-62, which showed 1.69% weight gain (entries 2 and 5 of Table 1). 1,3-propanediol itself, surprisingly, showed only negligible, if any, weight gain when NO was passed through it (entry 6 in Table 1). Thus, under experimental conditions, 1,3-propanediol did not react with nitric oxide.

Two samples were also prepared containing 800 ppm NO (from carrier HNC 157-62) and one sample containing 500 ppm NO (from carrier HNC 157-65) (entries 7-9 in Table 1). The IR spectra of the carriers did not show any additional bands after the reaction, possibly because of low amounts of nitrites and/or overlap with the carrier complex bands.

Mass spectral studies of the carrier HNC 157-62 and HNC 157-62 containing NO indicated that there was an increase in the intensity of the peak at m/e 104 in NO-containing carrier, compared to carrier without NO. The peak at m/e 104 was believed to be due to choline cation ($C_5H_{14}NO$). Phospholipon-90G may contain some free choline, and hence presence of the peak at 104 in the mass spectrum of the carrier was not surprising. However, the increase in the amount of choline after passage of NO was somewhat unexpected, although it is believed that nitric oxide catalyzes similar dephosphorylation of Phospholipon-90G releasing choline.

In conclusion, an increase in weight (0.56 to 1.69%) was observed when nitric oxide gas was passed through the carriers. 1,3-propanediol failed to gain any significant weight when nitric oxide was passed through it. HNC 157-69 (devoid of 1,3-propanediol) gained only 0.56% weight compared to 1.69% by its 1,3-propanediol containing analog HNC 157-62. The mass spectra of HNC 157-62 before and after passing NO indicated that the peak corresponding to choline at m/e 104 increased after the passage of NO, which suggests that phospholipon-90G may undergo NO-catalyzed dephosphorylation.

Example 3

This example illustrates non-invasive blood pressure measurements in mice using a composition in accordance with one embodiment of the invention.

Blood pressure in mice may be measured using blood volume changes in the mouse tail. Mice with normal tails (no clipping or short) were used in this study. Ages varied between 8 weeks and 24 weeks. This procedure uses the CODA non-invasive blood pressure system available from Kent Scientific (Torrington, Conn.) Mice weighing approximately 25 grams were restrained in plastic cylindrical housing with a nose come allowing the nose to protrude. Two tail cuffs provided occlusion and measurements. The O-cuff provided period occlusion while the VPR cuff provides volume-pressure recordings. The occlusion pressure and the recorded pressure were controlled automatically by the computer software.

Each measurement had 10 acclimation cycles and 20 measurement cycles once daily depending on the experimental parameters. The average blood pressure of male mice made over time was 136/88. In this study, blood pressure measurements of the control (base) mice and the test (treated) mice were made and averaged over a period of three days. The test composition comprised 800 ppm nitric oxide, which was applied over the upper back of the animal in a quantity that exceeded 50 mg. The blood pressures were recorded after each application and over 1 hour. The following results were obtained.

TABLE 2

Average Blood Pressure Reading

| Post Application | Control (Base) Product | Test (Treated) NO 800 ppm |
| --- | --- | --- |
| Time 0 | 167/123 | 140/91 |
| 1 Hour | 170/128 | 115/69 |

This study shows that the application of the test product is capable of reducing the blood pressure in a mouse to a significantly lower value.

TABLE 1

| Expt. No. | Carrier | Initial wt. g. | Final wt. g. | Time hr | Temp. °C. | Wt. Gain g | % Wt. gain |
| --- | --- | --- | --- | --- | --- | --- | --- |
| 1 | HNC 157-62 | 168.53 | 169.48 | 24 | 25 | 0.95 | 0.56 |
| 2 | HNC 157-62 | 171.31 | 174.21 | 48 | 25 | 2.90 | 1.69 |
| 3 | HNC 157-62 | 174.21* | 174.01 | 4 | 60 | −0.20 | −0.11 |
| 4 | HNC 157-65 | 171.66 | 172.98 | 24 | 25 | 1.32 | 0.77 |
| 5 | HNC 157-69 | 171.02 | 171.97 | 40 | 25 | 0.95 | 0.56 |
| 6 | 1,3-Propanediol | 178.81 | 178.97 | 40 | 25 | 0.16 | 0.09 |
| 7 | HNC 157-62 | 238.16 | 238.35 | 2 | 25 | 0.19 | 0.0798 (~800 ppm) |
| 8 | HNC 157-65 | 250.37 | 250.50 | 2 | 25 | 0.13 | 0.0519 (~500 ppm) |
| 9 | HNC 157-62 | 252.24 | 252.45 | 0.25 | 25 | 0.21 | 0.0833 (~800 ppm) |

Example 4

This example illustrates capillary blood flow measurements in humans using a composition similar to the ones described in the above examples.

Microcirculation properties of the skin were measured before and after application of a test product with nitric oxide. Measurements were made using a Moor® Laser Doppler instrument. Measurements were made at Day 1 before and immediately, 5 and 15 minutes after treatment.

The study participants were healthy females aged 30 to 55 years. They were in good health as determined by the medical history and were not taking any prescription medications. The test product was labeled as 800 ppm NO (nitric oxide). The study participants had 100 mg of the test product applied in a 2×2 sq. inch area on the forearm.

Laser Doppler was performed to measure increased stimulation of the micro-capillary blood flow to skin. The micro-circulation of the skin reflects the perfusion of the skin and the underlying tissue. The laser Doppler technique is the standard method to obtain dynamic measurement of capillary blood flow in clinical evaluation. Measurements can be made relatively rapidly and simultaneously at sites. In addition, temperature measurements may also be made at the same time.

A Moor Instruments DRT4 Laser Doppler Blood Flow Monitor (Devon, England) was used. The laser Doppler technique measures blood flow in the microcapillaries of the skin that are close to the skin surface and the blood flow in underlying arterioles and venules that help to regulate skin temperature. There are several parameter used to describe blood flow measured by this laser Doppler technique. These measurement parameters are defined by Moor Instruments Inc. and are listed below.

Flux: This parameter is related to the product of average speed and concentration of moving red blood cells in the tissue sample volume. It is the parameter most widely reported in Laser Doppler publication.

Conc: This parameter gives an indication of the number of moving red blood cells in the tissue sample volume.

Speed: This parameter gives an indication of the average speed of red blood cells moving in the tissue sample volume.

Temp: This is the probe temperature and where there is good thermal conduction between probe and tissue it reaches tissue temperature.

Because of the nature of blood flow in the capillaries and other small blood vessels, absolute flow units such as ml/minute cannot be expressed. Therefore, arbitrary units are used. Blood flow changes are defined as the percentage change from the baseline of these arbitrary units.

The procedure was as follows. The laser Doppler probe was attached onto the volar forearm. Control untreated skin readings (Baseline) were obtained for 15 minutes. The test product was then applied in the designated 2×2 sq. inch area and rubbed into the skin. Readings were obtained for 15 minutes.

The areas not used for evaluation include the first 15 seconds after starting data collection. Four 10 second areas in the baseline and test readings at each time point were randomly selected to obtain the mean averages which were then used in further analysis of the data.

The averaged data was compiled from the 4 study participants and the laser Doppler results are provided in the FIGURE. There was a significant difference observed in the control untreated skin and the skin treated with 800 ppm nitric oxide up to 15 minutes after application. The applied nitric oxide had an effect on the micro circulation of the skin at the applied level (100 mg in a 2×2 sq. inch area). The topical test product is capable of passing through the skin and affecting the microcirculation of the skin.

Example 5

This example illustrates delivery of nitric oxide formulations similar to those discussed herein in humans. In these studies, laser Doppler studies were performed on three human female subjects. As discussed below, all of the studies showed positive results consistent with a physiological effect of nitric oxide applied to the skin, passing through the skin and affecting the capillary circulation. The formulations used produce positive, almost immediate results when applied to the skin which, in these studies, was manifested by vasodilatation of the cutaneous vascular system.

While nitric oxide has many physiological effects, the purpose of these studies was to measure physiological effects that would be relatively easy to determine, and which would be noninvasive. Laser Doppler was selected for these studies because laser Doppler has a relatively large database that indicates that it is effective in determining an increase in microcirculation, i.e., circulation within the capillary bed immediately under the epidermal layer in the skin. Nitric oxide is capable of violating the capillary bed, and thus, laser Doppler was selected.

The formulation used in these studies contained nitric oxide dispersed in a lipid matrix. The nitric oxide was dispersed in the matrix and does not appear to be dissolved but remained intact, i.e., it appeared to diffuse into the skin as a molecule of nitric oxide rather than as atomic components or ions. Nitric oxide is a very rapid acting molecule, and these studies used a system that employed laser Doppler with a covered chamber. The formulation was placed into the chamber and then attached to the skin by an adhesive layer on the covering. This provided a stable measuring device as determined by multiple normal evaluations of the capillary blood flow without treatment of nitric oxide.

A known positive control, methyl nicotinate, was applied to the skin at a concentration of 1/10% in alcohol. There was a rapid response typical of the vasodilator. The vascular dynamics are such that when the blood vessels dilate physical parameters follow Bernoulli's law. This states that as one increases the diameter of a tube containing a liquid to flow will increase but the pressure and the speed of the liquid will decrease. The laser Doppler device accurately measured these parameters.

When nitric oxide was applied to the forearm of three human female subjects, it was observed that there was an immediate effect on the blood flow as soon as the formulation was applied. The speed of blood flow decreased, and the effects lasted over 15 minutes. There was no erythema and no discomfort to the subjects that was observed.

Thus, these studies showed that the nitric oxide in the lipid matrix when applied topically to the forearm, was able to penetrate the skin very rapidly and to interact with the underlying tissues. This is evidenced by the observation of vascular dilatation without erythema. Accordingly, it can be concluded from these studies that the formulation containing nitric oxide was effective in delivering nitric oxide through the skin in a physiologically active state.

In these studies, the participants were healthy females aged 30 to 55 years. They were in good health as determined by the medical history and were not taking any prescription medications. All study participants read and signed the informed consent statement prior to any study procedures being performed.

The test product was labeled as 10,000 ppm NO (nitric oxide). The study participants had 100 mg of the test product applied in a closed Hilltop chamber on the forearm.

Laser Doppler was performed to measure increased stimulation of the micro-capillary blood flow to skin. The micro-circulation of the skin reflected the perfusion of the skin and the underlying tissue. Laser Doppler is a standard method to obtain dynamic measurement of capillary blood flow in clinical evaluation. Measurements can be made relatively rapidly and simultaneously at sites. In addition, temperature measurements may also be made at the same time.

A Moor Instruments DRT4 Laser Doppler Blood Flow Monitor (Devon, England) was used in these studies. The laser Doppler technique measured blood flow in the micro-capillaries of the skin that are close to the skin surface and the blood flow in underlying arterioles and venules that help to regulate skin temperature. Because of the nature of blood flow in the capillaries and other small blood vessels, it is difficult to determine absolute flow units such as ml/minute. Therefore, arbitrary units were used in these experiments to determine relative changes. Blood flow changes were accordingly defined as the percentage change from the baseline using the arbitrary units.

Data was compiled from the three study participants and the laser Doppler studies and averaged. It observed that there was a significant difference observed in the control untreated skin and the skin treated with 10,000 ppm nitric oxide up to 15 minutes after application. The applied nitric oxide had an effect on the microcirculation of the skin at the applied level (100 mg in a lipid matrix). The formulation was determined to be capable of passing through the skin and affecting the microcirculation of the skin.

Example 6

This example illustrates a protocol used for determining the amount of nitric oxide released from various compositions of the present invention. The protocol is generally performed as follows:

1) Samples (within HNC carriers described herein) were maintained at either 4° C. or −20° C. until analyzed.

2) One at a time and before they were opened, samples were warmed to 37° C. (dry bath) in a controlled atmosphere of 1% $O_2$. They were opened and 150 microliters was removed and placed into 1.35 mL of PBS (pH 7.4, 25° C. and equilibrated to 13 micromolar $O_2$) in a small glass screw-cap vial minimizing headspace.

3) The vials were then subjected to 15 s of vortex agitation, caps opened and 1 mL quickly removed and immediately injected into a Sievers Nitric Oxide Analyzer reaction chamber containing 4 mL of deionized and distilled $H_2O$ equilibrated at 0% $O_2$ by a $N_2$ flow through gas and maintained at 37° C. by flow-through water jacket.

4) Peaks were analyzed by comparing values to a standard curve generated by injecting various concentrations of the NO donor 1-(hydroxy-NNO-azoxy)-L-proline (PROLI-NONOate). To standardize among samples, the area under the curve from 0 to 4 min was used for concentration determinations are expressed in moles of NO and have been corrected for the 2 dilutions (50×). As such, these values equal moles of NO/150 microliter matrix.

5) The authenticity of NO formation was validated by injecting 50 mM of the NO spin trap 2-(4-carboxyphenyl)-4,5-dihydro-4,4,5,5-tetramethyl-1H-imidazolyl-1-oxy-3-oxide (cPTIO) or by injecting sample into the reaction chamber containing 50 mM cPTIO and observing the absence of signal.

6) For each sample, the area under the curve from t=0 to t=4 min was calculated for concentration determinations. Calculations represent only the amount of NO released during this 4 min time span and thus do not represent the total amount of NO contained in the volume of matrix assessed (150 microliters). For each vial 3-5 independent determinations were performed (this means each injection represents removal of 150 microliters of matrix from the labeled vial, dilution in PBS and injection. As such, these were completely independent measurements from beginning to end.

TABLE 3

| Sample ID | Mean (millimoles NO) | Std Dev |
| --- | --- | --- |
| 1000 | 11.4 | 1.55 |
| 4000 | 60.7 | 1.70 |
| 7000 | 72.1 | 11.9 |
| 10000 | 127.9 | 11.3 |

In this table, the Sample ID numbers correspond to the amount of nitric oxide, in ppm, that was formulated in the composition (sample) tested.

Based on these results, the compositions tested here appeared to be effective in entrapping nitric oxide gas, and are effective in releasing the trapped gas in a measureable and significant way.

Example 7

This example illustrates delivery of nitric oxide formulations to five human subjects, using procedures and formulations similar to those discussed in Example 5. Each person served as their own control for the testing. A Moor Instruments Laser Doppler was used to determine circulation. All of these studies showed positive results consistent with a physiological effect of nitric oxide applied to the skin, passing through the skin and affecting the capillary circulation. The formulations used produce positive, almost immediate results when applied to the skin which, in these studies, was manifested by vasodilatation of the cutaneous vascular system.

For each subject, the following creams were applied: a negative control formulation (containing no NO), 0.010 gram of a 10,000 ppm NO formulation, 0.020 gram of a 10,000 ppm NO formulation, and a positive control formulation containing 0.1% methyl nicotinate. The formulations were prepared using procedures similar to those discussed in Example 1.

When nitric oxide was applied to the forearm of the subjects, it was observed that there was an immediate effect on the blood flow as soon as the formulation was applied. The speed of blood flow decreased, and the effects lasted over 15 minutes. There was no erythema and no discomfort to the subjects that was observed.

Data was compiled from the study participants and the laser Doppler studies and averaged. It observed that there was a significant difference observed in the control untreated skin (where no detectable vasodilation was observed), and the treatments involving 0.010 g of NO, 0.020 g of NO, and methyl nicotinate. For all three treatments, vasodilatation was observed, with somewhat greater vasodilatation for the 0.010 g formulation over the 0.02 g formulation. In addition, the amount of vasodilatation observed for the 0.01 g formulation of NO was generally similar to the amount of vasodilatation observed for methyl nicotinate.

Accordingly, these data demonstrate that NO as applied in a cream to the skin is able to penetrate the skin and affect bloodflow beneath the skin.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of", or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method, comprising:
    providing a sealed container containing a composition comprising molecular nitric oxide and phosphatidylcholine, wherein the sealed container contains less than about 20 mol % oxygen;
    unsealing the sealed container to allow access to the composition; and
    administering the composition to the skin of a subject having or at risk of neuropathic pain.

2. The method of claim 1, wherein the composition is a cream, gel, lotion, or ointment.

3. The method of claim 1, wherein the sealed container contains less than 5 mol % oxygen.

4. The method of claim 1, wherein the sealed container is substantially resistant to oxygen permeation.

5. The method of claim 1, wherein the sealed container is substantially resistant to nitrogen permeation.

6. The method of claim 1, wherein the sealed container is substantially resistant to carbon dioxide permeation.

7. The method of claim 1, wherein the sealed container is substantially watertight.

8. The method of claim 1, wherein the sealed container contains substantially no water.

9. The method of claim 1, wherein the sealed container has a relative humidity of less than about 10%.

10. The method of claim 1, wherein the sealed container contains a desiccant.

11. The method of claim 1, wherein the sealed container is a tube.

12. The method of claim 1, wherein the sealed container contains a metallic barrier.

13. The method of claim 1, wherein the sealed container contains a polymeric barrier.

14. The method of claim 1, wherein the composition comprises polyenylphosphatidylcholine.

15. The method of claim 1, wherein the composition comprises a liquid crystal structure.

16. The method of claim 1, wherein the composition comprises no more than about 250 ppm of water by weight of the composition.

17. The method of claim 1, wherein the phosphatidylcholine is present at at least about 0.25% by weight of the composition.

18. The method of claim 1, wherein the molecular nitric oxide is present at at least about 0.5% by weight of the composition without nitric oxide.

19. The method of claim 1, wherein the molecular nitric oxide is present within the composition as a gas.

20. The method of claim 1, wherein the molecular nitric oxide is bound by hydrogen bonds or van der Waals forces to the phosphatidylcholine.

* * * * *